US010202619B2

(12) United States Patent
Wu

(10) Patent No.: US 10,202,619 B2
(45) **Date of Patent: *Feb. 12, 2019**

(54) COMPOSITIONS AND METHODS DIRECTED TO CRISPR/CAS GENOMIC ENGINEERING SYSTEMS

(71) Applicant: System Biosciences, LLC, Mountain View, CA (US)

(72) Inventor: Fangting Wu, Mountain View, CA (US)

(73) Assignee: SYSTEM BIOSCIENCES, LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,282

(22) Filed: Oct. 5, 2015

(65) Prior Publication Data

US 2016/0138046 A1 May 19, 2016

Related U.S. Application Data

(63) Continuation of application No. 14/211,858, filed on Mar. 14, 2014, now Pat. No. 9,234,213.

(60) Provisional application No. 61/799,586, filed on Mar. 15, 2013.

(51) Int. Cl.

| | |
|---|---|
| ***C12N 9/22*** | (2006.01) |
| ***C12N 15/10*** | (2006.01) |
| ***C12N 15/11*** | (2006.01) |
| ***C12N 15/85*** | (2006.01) |
| ***C12N 15/90*** | (2006.01) |

(52) U.S. Cl.

CPC ............. *C12N 15/907* (2013.01); *C12N 9/22* (2013.01); *C12N 15/102* (2013.01); *C12N 15/11* (2013.01); *C12N 15/85* (2013.01); *C12N 2800/22* (2013.01)

(58) Field of Classification Search

None

See application file for complete search history.

(56) References Cited

U.S. PATENT DOCUMENTS

| | | | | |
|---|---|---|---|---|
| 5,571,690 | A | 11/1996 | Hecht | |
| 8,252,535 | B2 | 8/2012 | Biekle et al. | |
| 8,697,359 | B1 | 4/2014 | Zhang | |
| 8,771,945 | B1 | 7/2014 | Zhang | |
| 8,795,965 | B2 | 8/2014 | Zhang | |
| 8,865,406 | B2 | 10/2014 | Zhang et al. | |
| 8,871,445 | B2 | 10/2014 | Cong et al. | |
| 8,889,356 | B2 | 11/2014 | Zhang | |
| 8,889,418 | B2 | 11/2014 | Zhang et al. | |
| 8,895,308 | B1 | 11/2014 | Zhang et al. | |
| 8,906,616 | B2 | 12/2014 | Zhang et al. | |
| 9,234,213 | B2 * | 1/2016 | Wu ...................... | C12N 15/907 |
| 2010/0076057 | A1 | 3/2010 | Sontheimer et al. | |
| 2010/0093617 | A1 | 4/2010 | Barrangou et al. | |
| 2010/0104690 | A1 | 4/2010 | Barrangou et al. | |
| 2011/0002889 | A1 | 1/2011 | Barrangou et al. | |
| 2011/0189776 | A1 | 8/2011 | Terns et al. | |
| 2011/0300538 | A1 | 12/2011 | Barrangou et al. | |
| 2013/0011828 | A1 | 1/2013 | Barrangou et al. | |
| 2014/0068797 | A1 * | 3/2014 | Doudna ............... | C12N 15/102 800/18 |
| 2014/0170753 | A1 | 6/2014 | Zhang | |
| 2014/0179006 | A1 | 6/2014 | Zhang | |
| 2014/0179770 | A1 | 6/2014 | Zhang et al. | |
| 2014/0186843 | A1 | 7/2014 | Zhang et al. | |
| 2014/0186919 | A1 | 7/2014 | Zhang et al. | |
| 2014/0186958 | A1 | 7/2014 | Zhang et al. | |
| 2014/0189896 | A1 | 7/2014 | Zhang et al. | |
| 2014/0227787 | A1 | 8/2014 | Zhang | |
| 2014/0242664 | A1 | 8/2014 | Zhang et al. | |
| 2014/0242699 | A1 | 8/2014 | Zhang | |
| 2014/0248702 | A1 | 9/2014 | Cong et al. | |
| 2014/0256046 | A1 | 9/2014 | Zhang et al. | |
| 2014/0310830 | A1 | 10/2014 | Zhang et al. | |
| 2014/0342456 | A1 | 11/2014 | Mali et al. | |
| 2014/0342457 | A1 | 11/2014 | Mali et al. | |
| 2014/0342458 | A1 | 11/2014 | Mali et al. | |
| 2014/0356956 | A1 | 12/2014 | Church et al. | |
| 2014/0356958 | A1 | 12/2014 | Mali et al. | |
| 2014/0356959 | A1 | 12/2014 | Church et al. | |
| 2014/0357530 | A1 | 12/2014 | Zhang et al. | |
| 2015/0020223 | A1 | 1/2015 | Zhang et al. | |

FOREIGN PATENT DOCUMENTS

| | | |
|---|---|---|
| WO | 2002034771 A2 | 5/2002 |
| WO | 2006/055836 | 5/2006 |
| WO | 2007/025097 | 3/2007 |
| WO | 2008/052101 | 5/2008 |

(Continued)

OTHER PUBLICATIONS

Mali et al. (2013) RNA-Guided Human Genome Engineering via Cas9. Science, 339:823-826.*

Cong et al. (2013) Multiplex Genome Engineering Using CRISPR/Cas Systems. Science, 339:819-822, and supplementary materials, published online Jan. 3, 2013.*

Fath et al. (2011) Multiparameter RNA and Codon Optimization: A Standardized Tool to Assess and Enhance Autologous Mammalian Gene Expression. PLoS ONE, 6(3) :e17596, pp. 1-14.*

Rubinson et al. (2003) A lentivirus-based system to functionally silence genes in primary mammalian cells, stem cells and transgenic mice by RNA interference. Nature Genetics, 33(6):401-406 (Year: 2003).*

(Continued)

*Primary Examiner* — Neil P Hammell

(74) *Attorney, Agent, or Firm* — Dergosits & Noah LLP

(57) ABSTRACT

The invention relates to engineered CRISPR/Cas9 systems for genomic modification in mammalian cells. The present specification describes the design and testing of a polynucleotide encoding the *Streptococcus pyogenes* (*S. pyogenes*) Cas9 protein, where the nucleotide sequence has been optimized for expression in mammalian cells. The specification also describes all-in-one systems for RNA-guided genome engineering in mammalian cells, including human cells.

15 Claims, 26 Drawing Sheets

Specification includes a Sequence Listing.

(56) References Cited

FOREIGN PATENT DOCUMENTS

| | | |
|---|---|---|
| WO | 2008/122314 | 10/2008 |
| WO | 2010/011961 | 1/2010 |
| WO | 2010/054154 | 5/2010 |
| WO | 2010/075424 | 7/2010 |
| WO | 2012/054726 | 4/2012 |
| WO | 2012/164565 | 12/2012 |
| WO | 2013/176772 | 11/2013 |
| WO | 2014/093595 | 6/2014 |
| WO | 2014/093622 | 6/2014 |
| WO | 2014/093635 | 6/2014 |
| WO | 2014/093655 | 6/2014 |
| WO | 2014/093661 | 6/2014 |
| WO | 2014/093694 | 6/2014 |
| WO | 2014/093701 | 6/2014 |
| WO | 2014/093709 | 6/2014 |
| WO | 2014/093712 | 6/2014 |
| WO | 2014/093718 | 6/2014 |
| WO | 2014/099744 | 6/2014 |
| WO | 2014/099750 | 6/2014 |
| WO | 2014/197568 | 12/2014 |

OTHER PUBLICATIONS

Zhang et al. (2012) The effect of lentivirus-mediated expression of tumor necrosis factor related apoptosis-inducing ligand and shRNA against Bcl-2 on the growth of lymphoma cells. Leukemia & Lymphoma, 53(4):710-717 (Year: 2012).*

Sapranauskas et al. (2011) The *Streptococcus thermophilus* CRISPR/Cas system provides immunity in *Escherichia coli*. Nucleic Acids Research, 39(21):9275-9282 (Year: 2011).*

Bjork et al. (2010) A Transient Transgenic RNAi Strategy for Rapid Characterization of Gene Function during Embryonic Development. Plos One, 5(12):e14375, pp. 1-11 (Year: 2010).*

Barrangou, "RNA-mediated programmable DNA cleavage." Nature Biotechnology, 30(9), p. 836-838 (Sep. 2012).

Bassett et al., "Highly Efficient Targeted Mutagenesis of *Drosophila* with the CRISPR/Cas9 System," Cell Rep., 4 (1):220-228 (Jul. 11, 2013).

Bhaya et al., "CRISPR-Cas systems in bacteria and archaea: versatile small RNAs for adaptive defense and regulation," Annu. Rev. Genet. 45, 273 (2011).

Brouns, "A Swiss Army Knife of Immunity" Science 337: p. 808-809 (Aug. 17, 2012).

Burgess, "A CRISPR genome-editing tool." Nature Reviews-Genetics vol. 14 (Feb. 2013), published online Jan. 16, 2013.

Carr and Church, "Genome engineering," Nat. Biotechnol. 27, 1151 (2009).

Cho et al., "Targeted genome engineering in human cells with the Cas9 RNA-guided endonuclease," Nature Biotechnology 31:230-232 (epub Jan. 29, 2013).

Cong et al., "Multiplex Genome Engineering Using CRISPR/Cas Systems" Science 339(6121):819-823 (Feb. 15, 2013), epub Science Express (Jan. 3, 2013).

Gilbert et al., "CRISPR-mediated modular RNA-guided regulation of transcription in eukaryotes," Cell 154(2):442-451 (epub Jul. 11, 2013).

Hale et al., "Essential Features and Rational Design of CRISPR RNAs that Function with the Cas RAMP Module Complex to Cleave RNAs." Molecular Cell 45, p. 292-302 (print Feb. 10, 2012) [epub: Jan. 5, 2012].

Hwang et al. "Efficient genome editing in zebrafish using a CRISPR-Cas system." Nat. Biotechnol. advance online publication (Jan. 29, 2013).

Jiang et al, "RNA-guided editing of bacterial genomes using CRISPR-Cas systems," Nature Biotechnol., 31(3):233-239 (Mar. 2013; epub Jan. 29, 2013).

Jinek et al., (2012) "A Programmable Dual-RNA—Guided DNA Endonuclease in Adaptive Bacterial Immunity" Science 337(6096): p. 816-821 (print edition Aug. 17, 2012; epub Science Express, Jun. 28, 2012).

Jinek et al., RNA-programmed genome editing in human cells. (Jan. 29, 2013) eLife 2:e00471.

Koike-Yusa et al., "Genome-wide recessive genetic screening in mammalian cells with a lentiviral CRISPR-guide RNA library," Nature Biotechnology 32:267-273 (2014); epub Dec. 23, 2013.

Konermann et al., "Optical control of mammalian endogenous transcription and epigenetic states," Nature 500 (7463):472-476 (2013); epub Jul. 23, 2013.

Mäkinen et al., "Stable RNA interference: comparison of U6 and H1 promoters in endothelial cells and in mouse brain" J Gene Med. 8(4):433-441 (2006).

Mali et al., "RNA-Guided Human Genome Engineering via Cas9" Science 339(6121):823-826 (Feb. 15, 2013), epub Science Express (Jan. 3, 2013).

Mali et al., "CAS9 transcriptional activators for target specificity screening and paired nickases for cooperative genome engineering," Nature Biotechnology 31:833-838 (epub Aug. 1, 2013).

Makarova et al., "Evolution and classification of the CRISPR-Cas systems." Nat. Rev. Microbiol. 9, 467 (2011).

Perez-Pinera et al, "RNA-guided gene activation by CRISPR-Cas9—based transcription factors," Nature Methods 10:973-976 (epub Jul. 25, 2013).

Ran et al., "Double Nicking by RNA-Guided CRISPR Cas9 for Enhanced Genome Editing Specificity." Cell 154 (6):1380-1389 (Sep. 2013).

Segal, "Bacteria herald a new era of gene editing," eLife, Jan. 29, 2013; 2:e00563.

Shalem et al, "Genome-Scale CRISPR-Cas9 Knockout Screening in Human Cells," Science (Jan. 3, 2014) p. 84-87, epub Sciencexpress Dec. 12, 2013.

Shen et al., "Generation of gene-modified mice via Cas9/RNA-mediated gene targeting," Cell Res., 23(5):720-723 (May 2013; epub Apr. 2, 2013).

Sontheimer and Marraffini, "Slicer for DNA" Nature 468:p. 45-46 (in print Nov. 4, 2010; epub Nov. 3, 2010).

Sorek et al., "CRISPR—a widespread system that provides acquired resistance against phages in bacteria and archaea," Nature Reviews Microbiology 6:181-186 (Mar. 2008).

System Biosciences, Inc., pGreenFire™ Pathway Reporter Lentivectors Cat. # TR0XX Series User Manual, 19 pgs, dated Aug. 24, 2012.

System Biosciences, Inc., "PrecisionX Cas9 SmartNuclease™ Vector System, Catalog Nos. CASxxx series User Manual," ver.1, dated Apr. 22, 2013 (16 pages), retrieved from <http://www.systembio.com/downloads/Cas9-SmartNuclease-user-manual.pdf>.

System Biosciences, Inc., "PrecisionX Cas9 SmartNuclease™ RNA System, Catalog Nos. CAS5xxA-1 series User Manual," ver.2, dated Sep. 3, 2013 17 pages, retrieved from <http://www.systembio.com/downloads/CAS5xxA-1-gRNA_Cas9_mRNA.pdf>.

Terns and Terns, "CRISPR-based adaptive immune systems." Curr. Opin. Microbiol. 14, 321 (2011).

Wang et al., "One-step generation of mice carrying mutations in multiple genes by CRISPR/Cas—mediated genome engineering," Cell 153(4):910-918 (May 9, 2013; epub May 2, 2013).

Wiedenheft, Sternberg and Doudna, "RNA-guided genetic silencing systems in bacteria and archaea." Nature 482; p. 331-338 (print Feb. 15, 2012; epub Feb. 15, 2012).

Sanders "Cheap and easy technique to snip DNA could revolutionize gene therapy." Media Relations, Univ. of California Berkeley, NewsCenter website (dated Jan. 7, 2013). Retrieved from: <URL: http://newscenter.berkeley.edu/2013/01/07/cheap-and-easy-technique-to-snip-dna-could-revolutionize-gene-therapy/>.

Cain, "CRISPR genome editing," SciBX Science-Business eXchange 6(4); doi:10.1038/scibx.2013.77 (epub Jan. 31, 2013).

Collins, "Copy-editing the Genome: Extreme Personalized Medicine?" NIH Director's Blog (Jan. 22, 2013); retrieved from: <URL: http://directorsblog.nih.gov/copy-editing-the-genome-extreme-personalized-medicine/>; [retrieved on xx/xx/xx].

Leuty "QB3 powers new wave of bio startups," San Francisco Business Times (dated Sep. 14, 2012); retrieved from: <http://www.bizjournals.com/sanfrancisco/print-edition/2012/09/14/qb3-powers-new-wave-of-bio-startups.html? page=all>; [retrieved approximately Feb. 2013].

(56) References Cited

OTHER PUBLICATIONS

Addgene, "CRISPR/Cas Plasmids and Protocols," webpage retrieved from: <https://www.addgene.org/CRISPR/>; [retrieved on May 8, 2014].

Addgene, "CRISPR/Cas Plasmids for use in: Mammals," webpage retrieved from: <https://www.addgene.org/CRISPR/mammalian/ >; [retrieved on May 8, 2014].

National Center for Biotechnology Information (NCBI), National Institutes of Health, GenBank® Accession No. AAK33936.1, Priority to Apr. 1, 2014, 2 pages.

National Center for Biotechnology Information (NCBI), National Institutes of Health, GenBank® Accession No. NC_002737, Priority to Jun. 27, 2013, 1 page.

Sapranauskas et al. Nucleic Acids Research, 2011, 1-8.

U.S. Appl. No. 14/211,858, by Wu, entitled "Compositions and Methods Directed to CRISPR/Cas Genomic Engineering Systems," filed Mar. 14, 2014; Office Action dated Jun. 2, 2015.

Fath et al., "Multiparameter RNA and Codon Optimization: A Standardized Tool to Assess and Enhance Autologous Mammalian Gene Expression," PLoS ONE 6(3):e17956 (publ Mar. 3, 2011); 14 pages.

Cong et al., Science 339(6121):819-823 (print publication Feb. 15, 2013) with accompanying Supplemental Materials (34 pages).

Office Action for co-pending U.S. Appl. No. 14/211,858; dated Jun. 2, 2015.

Office Action, United States Patent and Trademark Office <www.uspto.gov>, U.S. Appl. No. 14/216,655 (now published US2014/0273226), communication mailing date Aug. 4, 2015.

Request for Ex Parte Reexamination for issued U.S. Pat. No. 9,738,908, Reexamination Control No. 90/014,003, Request filed in the USPTO on Aug. 24, 2017, 64 pages.

Gustafsson et al., "Codon Bias and Heterologous Protein Expression," Trends Biotechnol., 22(7):346-353 (2004).

USPTO Notice of Grant of Reexamination for issued U.S. Pat. No. 9,738,908, Reexamination Control No. 90/014,003, dated Sep. 29, 2017, 22 pages.

Reexamination Office Action for issued U.S. Pat. No. 9,738,908, Reexamination Control No. 90/014,003, dated Oct. 20, 2017, 27 pages.

Giselle N. Jacobson, et al. Quality Over Quantity: Optimizing Co-Translational Protein Folding with Non-"Optimal" Synonymous Codons. HHS Public Access 2016; 38: 102-110.

Vincent P. Mauro, et al. A Critical Analysis of Codon Optimization in Human Therapeutics. NIH Public Access, Author Manuscript. 2014; 604-613.

Tamir Tuller, et al. An Evolutionary Conserved Mechanism for Controlling the Efficiency of Protein Translation. Cell 2010; 344-354.

Chien-Hung Yu, et al. Codon Usage Influences the Local Rate of Translation Elongation to Regulate Co-Translational Protein Folding. Molecular Cell 2015 :59 ; 744-754.

Mian Zhou, et al. Non-Optimal Codon Usage Affects Expression, Structure and Function of Clock Protein FRQ. Letter 2013 : vol. 495 | Nature.

Nick J. Proudfoot. Transcriptional Termination in Mammals: Stopping the RNA Polymerase II Juggernaut. Summary, American Association for the Advancement of Science. 2016. vol. 352, Issue 6291.

Lee et al., "Regulation Mechanisms of Viral IRES-Driven Translation," Trends Microbiol., 25:546-561 (2017).

Szymczak-Workman et al., "Design and Construction of 2A Peptide-Linked Multicistronic Vectors," Cold Spring Harbor Protoc., 2012(2): 199-204 (2012).

Kimberly A. Dittmar, et al. Selective Charging of tRNA isoacceptors induced by amino-acid starvation. Scientific Report. European Molecular Biology Organization 2005; vol. 6, No. 2.

Kimberly A. Dittmar, et al. Tissue-Specific Differences in Human Transfer RNA Expression. Plos Genetics 2006; vol. 2; Issue 12.

Josua B. Plotkin, et al. Tissue-Specific Codon Usage and the Expression of Human Genes. PNAS 2004; vol. 101; No. 34.

Barbara Maertens, et al. Gene Optimization Mechanisms: A Multi-Gene Study Reveals a High Success Rate of Full-Length Human Proteins Expressed in *Escherichia coli*. Protein Science 2010; vol. 19:1312-1326.

Tamir Tuller, et al. An Evolutionarily Conserved Mechanism for Controlling the Efficiency of Protein Translation. Cell 2010; 344-354.

Eszterhas SK, Bouhassira EE, Martin DI, et al. Transcriptional interference by independently regulated genes occurs in any relative arrangement of the genes and is influenced by chromosomal integration position. Mol Cell Biol 2002;22:469-79.

Shearwin KE, Callen BP, Egan JB. Transcriptional interference—a crash course. Trends Genet 2005;21:339-45.

Watts JK, Corey DR. Silencing disease genes in the laboratory and the clinic. J Pathol 2012;226:365-79.

Meister G, Tuschl T. Mechanisms of gene silencing by double-stranded RNA. Nature 2004;431:343-9.

Prescott EM, Proudfoot NJ. Transcriptional collision between convergent genes in budding yeast. Proc Natl Arad Sci U S A 2002;99:8796-801.

Callen BP, Shearwin KE, Egan JB. Transcriptional interference between convergent promoters caused by elongation over the promoter. Mol Cell 2004;14:647-56.

Palmer AC, Ahlgren-Berg A, Egan JB, et al. Potent transcriptional interference by pausing of RNA polymerases over a downstream promoter. Mol Cell 2009;34:545-55.

Conte C, Dastugue B, Vaury C. Promoter competition as a mechanism of transcriptional interference mediated by retrotransposons. EMBO J 2002;21:3908-16.

Hu X, Eszterhas S, Pallazzi N, et al. Transcriptional interference among the murine beta-like globin genes. Blood 2007;109:2210-6.

Nie L, Das Thakur M, Wang Y, et al. Regulation of U6 promoter activity by transcriptional interference in viral vector-based RNAi. Genomics Proteomics Bioinformatics 2010;8:170-9.

Duttke SH. RNA polymerase III accurately initiates transcription from RNA polymerase II promoters in vitro. J Biol Chem 2014;289:20396-404.

Weiwei M, Zhenhua X, Feng L, et al. A significant increase of RNAi efficiency in human cells by the CMV enhancer with a tRNAlys promoter. J Biomed Biotechnol 2009;2009:514287.

Arimbasseri AG, Rijal K, Maraia RJ. Transcription termination by the eukaryotic RNA polymerase III. Biochim Biophys Acta 2013;1829:318-30.

Gao Z, Harwig A, Berkhout B, et al. Mutation of nucleotides around the +1 position of type 3 polymerase III promoters: The effect on transcriptional activity and start site usage. Transcription 2017;8:275-287.

Norrman K, Fischer Y, Bonnamy B, et al. Quantitative comparison of constitutive promoters in human ES cells. PLoS One 2010;5:e12413.

Kalderon D, Roberts BL, Richardson WD, et al. A short amino acid sequence able to specify nuclear location. Cell 1984;39:499-509.

Grossman E, Medalia O, Zwerger M. Functional architecture of the nuclear pore complex. Annu Rev Biophys 2012;41:557-84.

Roberts BL, Richardson WD, Smith AE. The effect of protein context on nuclear location signal function. Cell 1987;50:465-75.

Quax TE, Claassens NJ, Soll D, et al. Codon Bias as a Means to Fine-Tune Gene Expression. Mol Cell 2015;59:149-61.

Quax TE, Wolf YI, Koehorst JJ, et al. Differential translation tunes uneven production of operon-encoded proteins. Cell Rep 2013;4:938-44.

Ingolia NT, Lareau LF, Weissman JS. Ribosome profiling of mouse embryonic stem cells reveals the complexity and dynamics of mammalian proteomes. Cell 2011;147:789-802.

Gustafsson C, Minshull J, Govindarajan S, et al. Engineering genes for predictable protein expression. Protein Expr Purif 2012;83:37-46.

Zucchelli E, Pema M, Stornaiuolo A, et al. Codon Optimization Leads to Functional Impairment of RD114-TR Envelope Glycoprotein. Mol Ther Methods Clin Dev 2017;4:102-114.

Age Tats, et al. Preferred and avoided codon pairs in three domains of life. BioMed Central 2008; 9:463.

Gina Cannarozzi, et al. A role for Codon Order in Translation Dynamics. Cell 2010; 141, 355-367.

(56) References Cited

OTHER PUBLICATIONS

Cristina Pop, et al. Casual Signals Between Codon Bias, mRNA Structure, and the Efficiency of Translation and Elongation. Molecular Systems Biology 2014: 10:770.
Wenfeng Qian, et al. Balanced Codon usage Optimizes Eukaryotic Translational Efficiency. 2012:vol. 8 | Issue 3.
Robert Coleman, et al. Virus Attenuation by Genome-Scale Changes in Codon Pair Bias. Science 2008; vol. 320; 1784-1787.
Mark Welch, et al. You're One in a Googol: Optimizing Genes for Protein Expression. Interface Focus 2009; 6, S467-476.
Wenqi Ran, et al. Contribution of Speed and Accuracy to Translational Selection in Bacteria. Plos One. 2012; vol. 7 ; Issue 12.
Nathan Gould, et al. Computational Tools and Algorithms for Designing Customized Synthetic Genes. Frontiers in Bioengineering and Biotechnology 2014;vol. 2; Article 41.

* cited by examiner

EF1-hspCas9-H1-AAVS
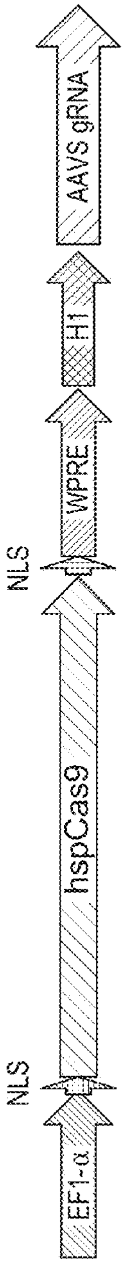
FIG. 3A
EF1-spCas9-mcherry-H1-AAVS
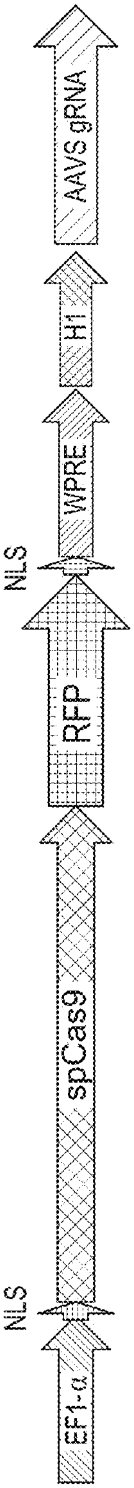
FIG. 3B
AAVS target sequence: GGGGCCACTAGGGACAGGAT (SEQ ID NO: 11)
FIG. 3C EGIP cell line tcagccgctaccccgaccacatgaagcagcacgacttcttcaagtccgccatgcccga
aggctacgtccaggagcgcaccatcttcttcaaggacgacggcaactacaagacctaa
GTCCCCTCCACCCCACAGTGGGGCCACTAGGGACAGGATTGGTGACAGAAAAGcgcgc
cgaggtgaagttcgagggcgacaccctggtgaaccgcatcgagctgaagggcatcgac
ttcaaggaggacggcaacat (SEQ ID NO: 12)

1. 100bp ladder
2. pZT-AAVS1-TALEN
3. EF1-spCas9-mcherry-H1-AAVS
4. EF1-hspCas9-H1-AAVS 1 2 3 4

500bp

100bp

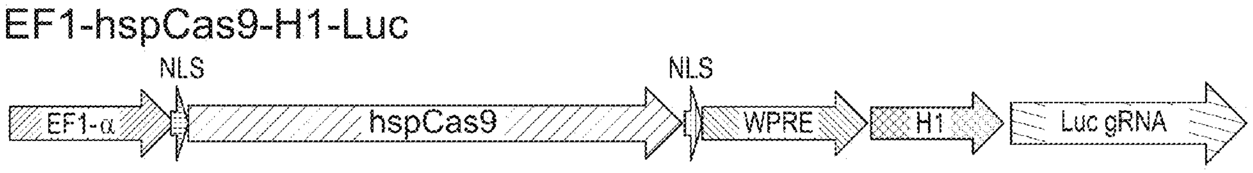
FIG. 6A
Luciferase gRNA sequences:
Luc gRNA1: GGCATGCGAGAATCTGACGC (SEQ ID NO: 13)
Luc gRNA2: CATGCCAGAGATCCTATTTT (SEQ ID NO: 14)
FIG. 6B
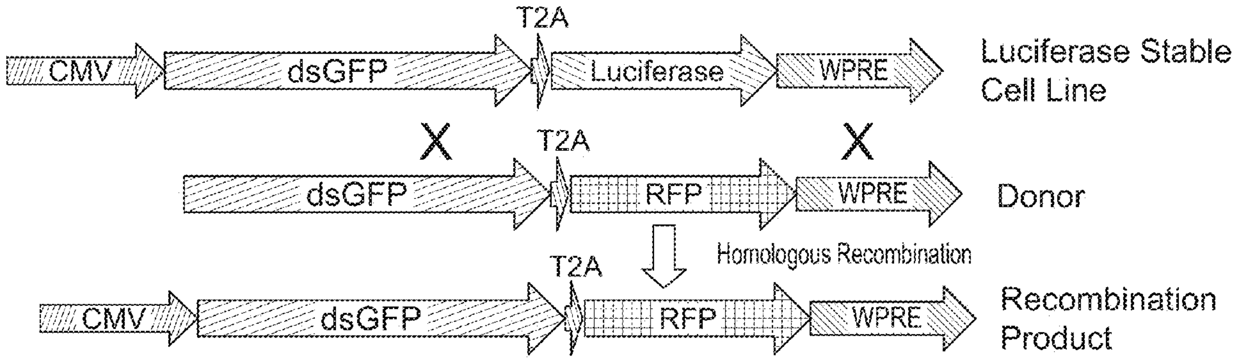
FIG. 6C atggctagtatgcagaaactgattagtgaagaggacctgATGGCTCCCAAGAAGAAGCGAAAGG
TGGGCATCCACGGCGTGCCCGCTGCCGACAAAAAGTATAGTATCGGACTGGATATTGGCACTAA
CAGCGTGGGATGGGCCGTCATCACCGACGAGTACAAAGTGCCAAGCAAGAAGTTCAAGGTCCTG
GGAAACACCGATAGACACAGTATCAAGAAAAATCTGATTGGAGCCCTGCTGTTCGACTCAGGGG
AGACAGCTGAAGCAACTAGGCTGAAAAGAACAGCTAGGAGACGGTATACTCGCCGAAAGAATCG
GATCTGCTACCTCCAGGAGATTTTCTCCAACGAAATGGCCAAGGTGGACGATAGTTTCTTTCAT
CGCCTGGAGGAATCATTCCTGGTCGAGGAAGATAAGAAACACGAGAGGCATCCCATCTTTGGCA
ACATTGTGGACGAGGTCGCTTATCACGAAAAGTACCCTACAATCTATCATCTGCGGAAGAAACT
GGTGGACAGCACTGATAAGGCAGACCTGCGCCTGATCTATCTGGCCCTGGCTCACATGATTAAG
TTCAGGGGGCATTTTCTGATCGAGGGCGATCTGAACCCAGACAATTCCGATGTGGACAAGCTGT
TCATCCAGCTGGTCCAGACATACAATCAGCTGTTTGAGGAAAACCCCATTAATGCATCTGGGGT
GGACGCAAAAGCCATCCTGAGTGCCAGACTGTCTAAGAGTAGGAGACTGGAGAACCTGATCGCT
CAGCTGCCAGGCGAAAAGAAAAACGGCCTGTTTGGAAATCTGATTGCACTGTCACTGGGACTGA
CCCCCAACTTCAAGAGCAATTTTGATCTGGCCGAGGACGCTAAGCTCCAGCTGAGCAAGGACAC
CTACGACGATGACCTGGATAACCTGCTGGCTCAGATCGGCGATCAGTACGCAGACCTGTTCCTG
GCCGCTAAGAATCTGTCTGACGCCATCCTGCTGAGTGATATTCTGAGAGTGAACACCGAGATTA
CAAAAGCCCCCCTGTCAGCTAGCATGATCAAGAGATATGACGAGCACCATCAGGATCTGACCCT
GCTGAAGGCTCTGGTGCGGCAGCAGCTGCCTGAGAAGTACAAAGAAATCTTCTTTGATCAGAGC
AAGAATGGGTACGCCGGCTATATTGACGGCGGAGCTTCCCAGGAGGAGTTCTACAAGTTTATCA
AACCTATTCTGGAGAAGATGGACGGCACTGAGGAACTGCTGGTGAAACTGAATCGGGAAGACCT
GCTGCGGAAGCAGCGCACCTTCGATAACGGCAGCATCCCTCACCAGATTCATCTGGGAGAGCTG
CACGCAATCCTGCGGCGCCAGGAAGACTTCTACCCATTTCTGAAGGATAACCGGGAGAAGATCG
AAAAAATTCTGACTTTCCGCATCCCCTACTATGTGGGGCCTCTGGCAAGAGGCAATTCCCGGTT
TGCCTGGATGACCCGCAAGTCTGAGGAAACAATCACTCCCTGGAACTTCGAGGAAGTGGTCGAT
AAGGGCGCTTCCGCACAGTCTTTCATTGAGAGGATGACAAATTTTGACAAGAACCTGCCAAATG
AAAAAGTGCTGCCCAAGCACAGCCTGCTGTACGAGTATTTCACCGTCTATAACGAACTGACAAA

FIG. 10A

GGTGAAATACGTCACTGAGGGCATGAGAAAGCCTGCCTTCCTGTCCGGAGAACAGAAGAAAGCT
ATCGTGGACCTGCTGTTTAAAACCAATCGGAAGGTGACAGTCAAGCAGCTGAAAGAGGACTACT
TCAAGAAAATTGAATGTTTCGATTCTGTGGAGATCAGTGGGGTCGAAGACAGGTTTAACGCCTC
TCTGGGCACCTACCACGATCTGCTGAAGATCATTAAGGATAAAGACTTCCTGGACAACGAGGAA
AATGAGGACATCCTGGAGGACATTGTGCTGACCCTGACACTGTTTGAGGATCGGGAAATGATCG
AGGAACGCCTGAAGACCTACGCCCATCTGTTCGATGACAAAGTGATGAAACAGCTGAAGCGAAG
GAGATACACTGGGTGGGGCCGACTGAGCAGGAAGCTGATCAATGGCATTCGCGACAAACAGAGT
GGAAAGACAATCCTGGACTTTCTGAAGTCAGATGGCTTCGCTAACAGGAATTTTATGCAGCTGA
TTCACGATGACTCTCTGACTTTCAAAGAGGACATCCAGAAGGCACAGGTGTCCGGACAGGGGGA
CTCTCTGCACGAGCATATCGCAAACCTGGCCGGGAGCCCTGCCATCAAGAAAGGCATCCTCCAG
ACCGTGAAGGTGGTGGACGAGCTGGTGAAAGTCATGGGAAGACATAAGCCAGAAAACATCGTGA
TTGAGATGGCCAGGGAGAATCAGACCACACAGAAAGGGCAGAAGAACTCTCGGGAGCGCATGAA
ACGCATCGAGGAAGGAATTAAGGAACTGGGGAGTCAGATCCTGAAAGAGCACCCCGTGGAAAAC
ACACAGCTCCAGAATGAGAAGCTGTATCTGTACTACCTCCAGAATGGCCGCGATATGTACGTGG
ACCAGGAGCTGGATATTAACCGACTGTCAGATTATGACGTGGATCATATCGTCCCACAGTCATT
CCTGAAAGATGACAGCATTGACAATAAGGTGCTGACCCGCAGCGACAAAAACCGAGGAAAGAGT
GATAATGTCCCCTCAGAGGAAGTGGTCAAGAAAATGAAGAACTACTGGAGGCAGCTGCTGAATG
CCAAACTGATCACCCAGCGAAAGTTTGATAACCTGACAAAAGCTGAGAGGGGGGGCCTGTCCGA
ACTGGACAAAGCAGGCTTCATCAAGCGACAGCTGGTGGAGACaAGGCAGATCACAAAGCACGTC
GCTCAGATCCTGGACAGCAGGATGAACACCAAGTACGATGAGAATGACAAACTGATCCGGGAAG
TGAAGGTCATTACACTGAAGTCAAAACTGGTGAGCGACTTTAGGAAAGATTTCCAGTTCTACAA
GGTCAGAGAGATCAACAACTACCACCATGCTCATGACGCATACCTGAACGCAGTGGTCGGGACT
GCCCTGATTAAGAAATACCCTAAACTGGAGTCTGAGTTCGTGTACGGCGACTATAAGGTGTACG
ATGTCAGAAAAATGATCGCCAAGAGCGAGCAGGAAATTGGCAAAGCCACCGCTAAGTATTTCTT
TTACTCCAACATCATGAATTTCTTTAAGACTGAGATCACCCTGGCAAATGGCGAAATCCGAAAG
AGGCCACTGATTGAGACTAACGGAGAGACaGGGGAAATCGTGTGGGACAAAGGAAGAGATTTTG

FIG. 10B

CTACCGTGCGGAAGGTCCTGAGTATGCCCCAAGTGAATATTGTCAAGAAAACAGAGGTGCAGAC
TGGAGGGTTCAGTAAGGAATCAATTCTGCCTAAACGCAACAGCGATAAGCTGATCGCCCGAAAG
AAAGACTGGGACCCCAAGAAGTATGGCGGATTCGACTCCCCAACCGTGGCTTACTCTGTCCTGG
TGGTCGCAAAGGTGGAGAAGGGAAAAAGCAAGAAACTGAAATCCGTCAAGGAACTGCTGGGGAT
CACAATTATGGAGAGGAGCAGCTTCGAAAAGAATCCTATCGATTTTCTGGAGGCCAAAGGGTAT
AAGGAAGTGAAGAAAGACCTGATCATCAAGCTGCCAAAGTACTCTCTGTTTGAGCTGGAAAACG
GCAGAAAGCGGATGCTGGCAAGTGCCGGCGAGCTGCAAAAAGGAAATGAACTGGCCCTGCCCTC
AAAGTACGTGAACTTCCTGTATCTGGCTAGCCACTACGAGAAGCTGAAAGGCTCCCCTGAGGAT
AACGAACAGAAACAGCTGTTTGTGGAGCAGCACAAGCATTATCTGGACGAGATCATTGAACAGA
TTAGCGAGTTCTCCAAACGCGTGATCCTGGCTGACGCAAATCTGGATAAGGTCCTGTCTGCATA
CAACAAACACAGGGACAAGCCAATCAGAGAGCAGGCCGAAAATATCATTCATCTGTTCACTCTG
ACCAACCTGGGAGCCCCCGCAGCCTTCAAGTATTTTGACACTACCATCGATCGCAAACGATACA
CAAGCACTAAGGAGGTGCTGGATGCTACCCTGATCCACCAGAGCATTACTGGGCTGTACGAGAC
AAGGATCGACCTGTCCCAGCTGGGGGGAGACAAACGCCCAGCCGCCACCAAGAAAGCAGGACAG
GCAAAGAAGAAGAAGTGA (SEQ ID NO: 1)

FIG. 10C

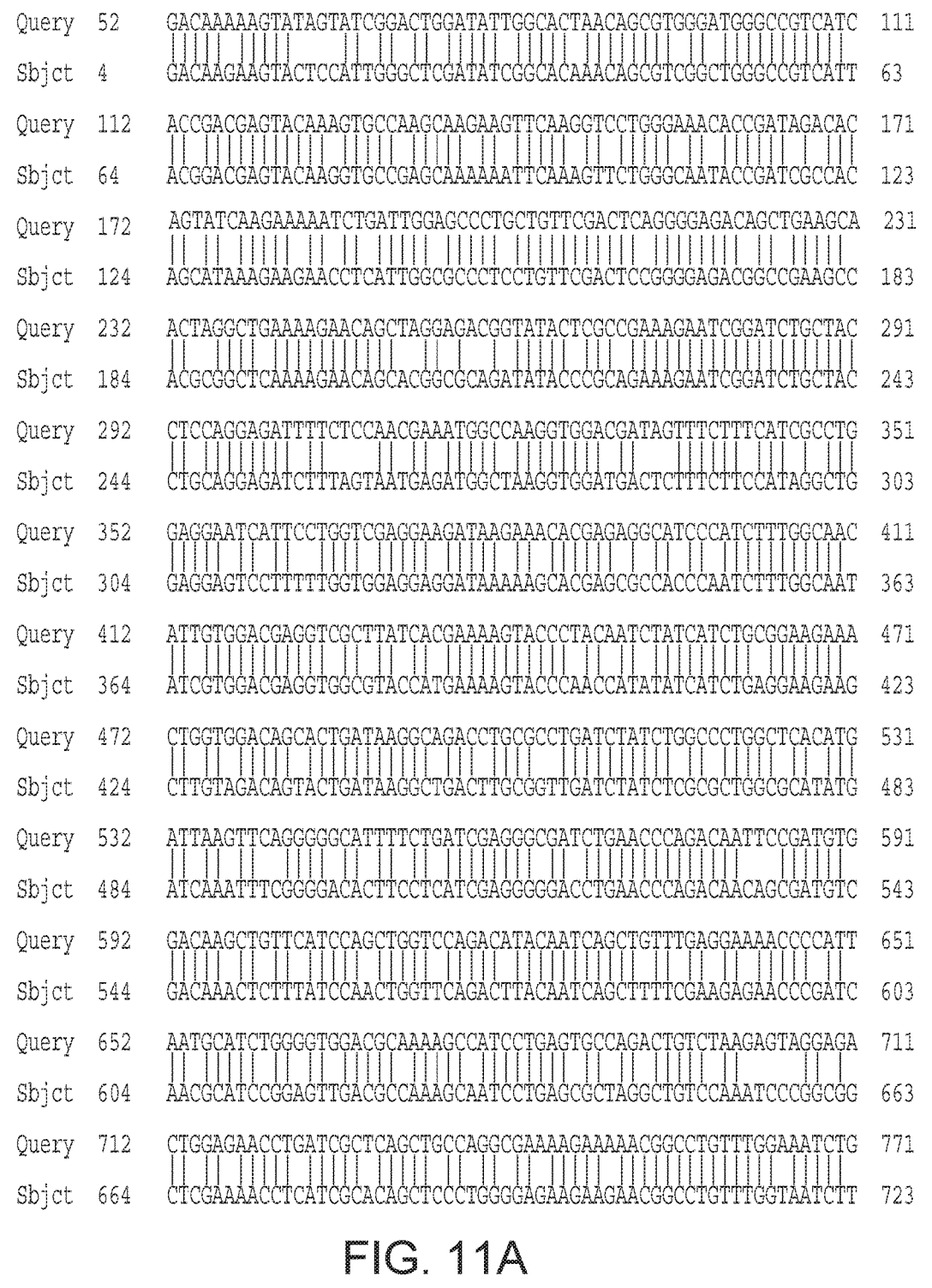

```
Query  52   GACAAAAAGTATAGTATCGGACTGGATATTGGCACTAACAGCGTGGGATGGGCCGTCATC  111
Sbjct  4    GACAAGAAGTACTCCATTGGGCTCGATATCGGCACAAACAGCGTCGGCTGGGCCGTCATT  63

Query  112  ACCGACGAGTACAAAGTGCCAAGCAAGAAGTTCAAGGTCCTGGGAAACACCGATAGACAC  171
Sbjct  64   ACGGACGAGTACAAGGTGCCGAGCAAAAAATTCAAAGTTCTGGGCAATACCGATCGCCAC  123

Query  172  AGTATCAAGAAAAATCTGATTGGAGCCCTGCTGTTCGACTCAGGGGAGACAGCTGAAGCA  231
Sbjct  124  AGCATAAAGAAGAACCTCATTGGCGCCCTCCTGTTCGACTCCGGGGAGACGGCCGAAGCC  183

Query  232  ACTAGGCTGAAAAGAACAGCTAGGAGACGGTATACTCGCCGAAAGAATCGGATCTGCTAC  291
Sbjct  184  ACGCGGCTCAAAAGAACAGCACGGCGCAGATATACCCGCAGAAAGAATCGGATCTGCTAC  243

Query  292  CTCCAGGAGATTTTCTCCAACGAAATGGCCAAGGTGGACGATAGTTTCTTTCATCGCCTG  351
Sbjct  244  CTGCAGGAGATCTTTAGTAATGAGATGGCTAAGGTGGATGACTCTTTCTTCCATAGGCTG  303

Query  352  GAGGAATCATTCCTGGTCGAGGAAGATAAGAAACACGAGAGGCATCCCATCTTTGGCAAC  411
Sbjct  304  GAGGAGTCCTTTTTGGTGGAGGAGGATAAAAAGCACGAGCGCCACCCAATCTTTGGCAAT  363

Query  412  ATTGTGGACGAGGTCGCTTATCACGAAAAGTACCCTACAATCTATCATCTGCGGAAGAAA  471
Sbjct  364  ATCGTGGACGAGGTGGCGTACCATGAAAAGTACCCAACCATATATCATCTGAGGAAGAAG  423

Query  472  CTGGTGGACAGCACTGATAAGGCAGACCTGCGCCTGATCTATCTGGCCCTGGCTCACATG  531
Sbjct  424  CTTGTAGACAGTACTGATAAGGCTGACTTGCGGTTGATCTATCTCGCGCTGGCGCATATG  483

Query  532  ATTAAGTTCAGGGGGCATTTTCTGATCGAGGGCGATCTGAACCCAGACAATTCCGATGTG  591
Sbjct  484  ATCAAATTTCGGGGACACTTCCTCATCGAGGGGGACCTGAACCCAGACAACAGCGATGTC  543

Query  592  GACAAGCTGTTCATCCAGCTGGTCCAGACATACAATCAGCTGTTTGAGGAAAACCCCATT  651
Sbjct  544  GACAAACTCTTTATCCAACTGGTTCAGACTTACAATCAGCTTTTCGAAGAGAACCCGATC  603

Query  652  AATGCATCTGGGGTGGACGCAAAAGCCATCCTGAGTGCCAGACTGTCTAAGAGTAGGAGA  711
Sbjct  604  AACGCATCCGGAGTTGACGCCAAAGCAATCCTGAGCGCTAGGCTGTCCAAATCCCGGCGG  663

Query  712  CTGGAGAACCTGATCGCTCAGCTGCCAGGCGAAAAGAAAAACGGCCTGTTTGGAAATCTG  771
Sbjct  664  CTCGAAAACCTCATCGCACAGCTCCCTGGGGAGAAGAAGAACGGCCTGTTTGGTAATCTT  723
```

FIG. 11A

```
Query  772   ATTGCACTGTCACTGGGACTGACCCCCAACTTCAAGAGCAATTTTGATCTGGCCGAGGAC  831
Sbjct  724   ATCGCCCTGTCACTCGGGCTGACCCCCAACTTTAAATCTAACTTCGACCTGGCCGAAGAT  783

Query  832   GCTAAGCTCCAGCTGAGCAAGGACACCTACGACGATGACCTGGATAACCTGCTGGCTCAG  891
Sbjct  784   GCCAAGCTTCAACTGAGCAAAGACACCTACGATGATGATCTCGACAATCTGCTGGCCCAG  843

Query  892   ATCGGCGATCAGTACGCAGACCTGTTCCTGGCCGCTAAGAATCTGTCTGACGCCATCCTG  951
Sbjct  844   ATCGGCGACCAGTACGCAGACCTTTTTTTGGCGGCAAAGAACCTGTCAGACGCCATTCTG  903

Query  952   CTGAGTGATATTCTGAGAGTGAACACCGAGATTACAAAAGCCCCCCTGTCAGCTAGCATG  1011
Sbjct  904   CTGAGTGATATTCTGCGAGTGAACACGGAGATCACCAAAGCTCCGCTGAGCGCTAGTATG  963

Query  1012  ATCAAGAGATATGACGAGCACCATCAGGATCTGACCCTGCTGAAGGCTCTGGTGCGGCAG  1071
Sbjct  964   ATCAAGCGCTATGATGAGCACCACCAAGACTTGACTTTGCTGAAGGCCCTTGTCAGACAG  1023

Query  1072  CAGCTGCCTGAGAAGTACAAAGAAATCTTCTTTGATCAGAGCAAGAATGGGTACGCCGGC  1131
Sbjct  1024  CAACTGCCTGAGAAGTACAAGGAAATTTTCTTCGATCAGTCTAAAAATGGCTACGCCGGA  1083

Query  1132  TATATTGACGGCGGAGCTTCCCAGGAGGAGTTCTACAAGTTTATCAAACCTATTCTGGAG  1191
Sbjct  1084  TACATTGACGGCGGAGCAAGCCAGGAGGAATTTTACAAATTTATTAAGCCCATCTTGGAA  1143

Query  1192  AAGATGGACGGCACTGAGGAACTGCTGGTGAAACTGAATCGGGAAGACCTGCTGCGGAAG  1251
Sbjct  1144  AAAATGGACGGCACCGAGGAGCTGCTGGTAAAGCTTAACAGAGAAGATCTGTTGCGCAAA  1203

Query  1252  CAGCGCACCTTCGATAACGGCAGCATCCCTCACCAGATTCATCTGGGAGAGCTGCACGCA  1311
Sbjct  1204  CAGCGCACTTTCGACAATGGAAGCATCCCCCACCAGATTCACCTGGGCGAACTGCACGCT  1263

Query  1312  ATCCTGCGGCGCCAGGAAGACTTCTACCCATTTCTGAAGGATAACCGGGAGAAGATCGAA  1371
Sbjct  1264  ATCCTCAGGCGGCAAGAGGATTTCTACCCCTTTTTGAAAGATAACAGGGAAAAGATTGAG  1323

Query  1372  AAAATTCTGACTTTCCGCATCCCCTACTATGTGGGGCCTCTGGCAAGAGGCAATTCCCGG  1431
Sbjct  1324  AAAATCCTCACATTTCGGATACCCTACTATGTAGGCCCCCTCGCCCGGGGAAATTCCAGA  1383

Query  1432  TTTGCCTGGATGACCCGCAAGTCTGAGGAAACAATCACTCCCTGGAACTTCGAGGAAGTG  1491
Sbjct  1384  TTCGCGTGGATGACTCGCAAATCAGAAGAGACCATCACTCCCTGGAACTTCGAGGAAGTC  1443
```

FIG. 11B

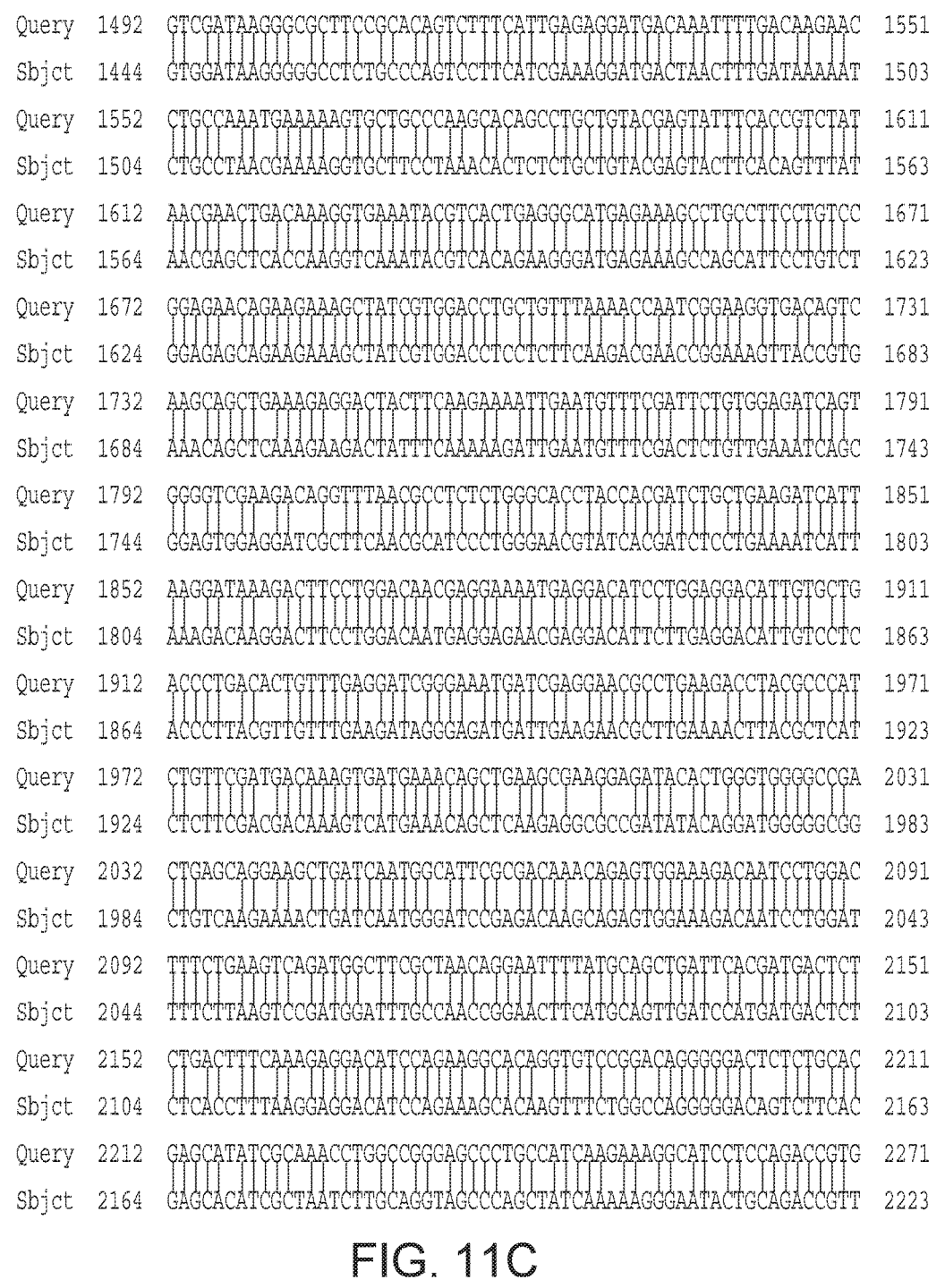

```
Query  1492  GTCGATAAGGGCGCTTCCGCACAGTCTTTCATTGAGAGGATGACAAATTTTGACAAGAAC  1551
Sbjct  1444  GTGGATAAGGGGGCCTCTGCCCAGTCCTTCATCGAAAGGATGACTAACTTTGATAAAAAT  1503

Query  1552  CTGCCAAATGAAAAAGTGCTGCCCAAGCACAGCCTGCTGTACGAGTATTTCACCGTCTAT  1611
Sbjct  1504  CTGCCTAACGAAAAGGTGCTTCCTAAACACTCTCTGCTGTACGAGTACTTCACAGTTTAT  1563

Query  1612  AACGAACTGACAAAGGTGAAATACGTCACTGAGGGCATGAGAAAGCCTGCCTTCCTGTCC  1671
Sbjct  1564  AACGAGCTCACCAAGGTCAAATACGTCACAGAAGGGATGAGAAAGCCAGCATTCCTGTCT  1623

Query  1672  GGAGAACAGAAGAAAGCTATCGTGGACCTGCTGTTTAAAACCAATCGGAAGGTGACAGTC  1731
Sbjct  1624  GGAGAGCAGAAGAAAGCTATCGTGGACCTCCTCTTCAAGACGAACCGGAAAGTTACCGTG  1683

Query  1732  AAGCAGCTGAAAGAGGACTACTTCAAGAAAATTGAATGTTTCGATTCTGTGGAGATCAGT  1791
Sbjct  1684  AAACAGCTCAAAGAAGACTATTTCAAAAAGATTGAATGTTTCGACTCTGTTGAAATCAGC  1743

Query  1792  GGGGTCGAAGACAGGTTTAACGCCTCTCTGGGCACCTACCACGATCTGCTGAAGATCATT  1851
Sbjct  1744  GGAGTGGAGGATCGCTTCAACGCATCCCTGGGAACGTATCACGATCTCCTGAAAATCATT  1803

Query  1852  AAGGATAAAGACTTCCTGGACAACGAGGAAAATGAGGACATCCTGGAGGACATTGTGCTG  1911
Sbjct  1804  AAAGACAAGGACTTCCTGGACAATGAGGAGAACGAGGACATTCTTGAGGACATTGTCCTC  1863

Query  1912  ACCCTGACACTGTTTGAGGATCGGGAAATGATCGAGGAACGCCTGAAGACCTACGCCCAT  1971
Sbjct  1864  ACCCTTACGTTGTTTGAAGATAGGGAGATGATTGAAGAACGCTTGAAAACTTACGCTCAT  1923

Query  1972  CTGTTCGATGACAAAGTGATGAAACAGCTGAAGCGAAGGAGATACACTGGGTGGGGCCGA  2031
Sbjct  1924  CTCTTCGACGACAAAGTCATGAAACAGCTCAAGAGGCGCCGATATACAGGATGGGGGCGG  1983

Query  2032  CTGAGCAGGAAGCTGATCAATGGCATTCGCGACAAACAGAGTGGAAAGACAATCCTGGAC  2091
Sbjct  1984  CTGTCAAGAAAACTGATCAATGGGATCCGAGACAAGCAGAGTGGAAAGACAATCCTGGAT  2043

Query  2092  TTTCTGAAGTCAGATGGCTTCGCTAACAGGAATTTTATGCAGCTGATTCACGATGACTCT  2151
Sbjct  2044  TTTCTTAAGTCCGATGGATTTGCCAACCGGAACTTCATGCAGTTGATCCATGATGACTCT  2103

Query  2152  CTGACTTTCAAAGAGGACATCCAGAAGGCACAGGTGTCCGGACAGGGGGACTCTCTGCAC  2211
Sbjct  2104  CTCACCTTTAAGGAGGACATCCAGAAAGCACAAGTTTCTGGCCAGGGGGACAGTCTTCAC  2163

Query  2212  GAGCATATCGCAAACCTGGCCGGGAGCCCTGCCATCAAGAAAGGCATCCTCCAGACCGTG  2271
Sbjct  2164  GAGCACATCGCTAATCTTGCAGGTAGCCCAGCTATCAAAAAGGGAATACTGCAGACCGTT  2223
```

FIG. 11C

```
Query  2272  AAGGTGGTGGACGAGCTGGTGAAAGTCATGGGAAGACATAAGCCAGAAAACATCGTGATT  2331
Sbjct  2224  AAGGTCGTGGATGAACTCGTCAAAGTAATGGGAAGGCATAAGCCCGAGAATATCGTTATC  2283

Query  2332  GAGATGGCCAGGGAGAATCAGACCACACAGAAAGGGCAGAAGAACTCTCGGGAGCGCATG  2391
Sbjct  2284  GAGATGGCCCGAGAGAACCAAACTACCCAGAAGGGACAGAAGAACAGTAGGGAAAGGATG  2343

Query  2392  AAACGCATCGAGGAAGGAATTAAGGAACTGGGGAGTCAGATCCTGAAAGAGCACCCCGTG  2451
Sbjct  2344  AAGAGGATTGAAGAGGGTATAAAAGAACTGGGGTCCCAAATCCTTAAGGAACACCCAGTT  2403

Query  2452  GAAAACACACAGCTCCAGAATGAGAAGCTGTATCTGTACTACCTCCAGAATGGCCGCGAT  2511
Sbjct  2404  GAAAACACCCAGCTTCAGAATGAGAAGCTCTACCTGTACTACCTGCAGAACGGCAGGGAC  2463

Query  2512  ATGTACGTGGACCAGGAGCTGGATATTAACCGACTGTCAGATTATGACGTGGATCATATC  2571
Sbjct  2464  ATGTACGTGGATCAGGAACTGGACATCAATCGGCTCTCCGACTACGACGTGGATCATATC  2523

Query  2572  GTCCCACAGTCATTCCTGAAAGATGACAGCATTGACAATAAGGTGCTGACCCGCAGCGAC  2631
Sbjct  2524  GTGCCCCAGTCTTTTCTCAAAGATGATTCTATTGATAATAAAGTGTTGACAAGATCCGAT  2583

Query  2632  AAAAACCGAGGAAAGAGTGATAATGTCCCCTCAGAGGAAGTGGTCAAGAAAATGAAGAAC  2691
Sbjct  2584  AAAAATAGAGGGAAGAGTGATAACGTCCCCTCAGAAGAAGTTGTCAAGAAAATGAAAAAT  2643

Query  2692  TACTGGAGGCAGCTGCTGAATGCCAAACTGATCACCCAGCGAAAGTTTGATAACCTGACA  2751
Sbjct  2644  TATTGGCGGCAGCTGCTGAACGCCAAACTGATCACACAACGGAAGTTCGATAATCTGACT  2703

Query  2752  AAAGCTGAGAGGGGGGGCCTGTCCGAACTGGACAAAGCAGGCTTCATCAAGCGACAGCTG  2811
Sbjct  2704  AAGGCTGAACGAGGTGGCCTGTCTGAGTTGGATAAAGCCGGCTTCATCAAAAGGCAGCTT  2763

Query  2812  GTGGAGACAAGGCAGATCACAAAGCACGTCGCTCAGATCCTGGACAGCAGGATGAACACC  2871
Sbjct  2764  GTTGAGACACGCCAGATCACCAAGCACGTGGCCCAAATTCTCGATTCACGCATGAACACC  2823

Query  2872  AAGTACGATGAGAATGACAAACTGATCCGGGAAGTGAAGGTCATTACACTGAAGTCAAAA  2931
Sbjct  2824  AAGTACGATGAAAATGACAAACTGATTCGAGAGGTGAAAGTTATTACTCTGAAGTCTAAG  2883

Query  2932  CTGGTGAGCGACTTTAGGAAAGATTTCCAGTTCTACAAGGTCAGAGAGATCAACAACTAC  2991
Sbjct  2884  CTGGTCTCAGATTTCAGAAAGGACTTTCAGTTTTATAAGGTGAGAGAGATCAACAATTAC  2943
```

FIG. 11D

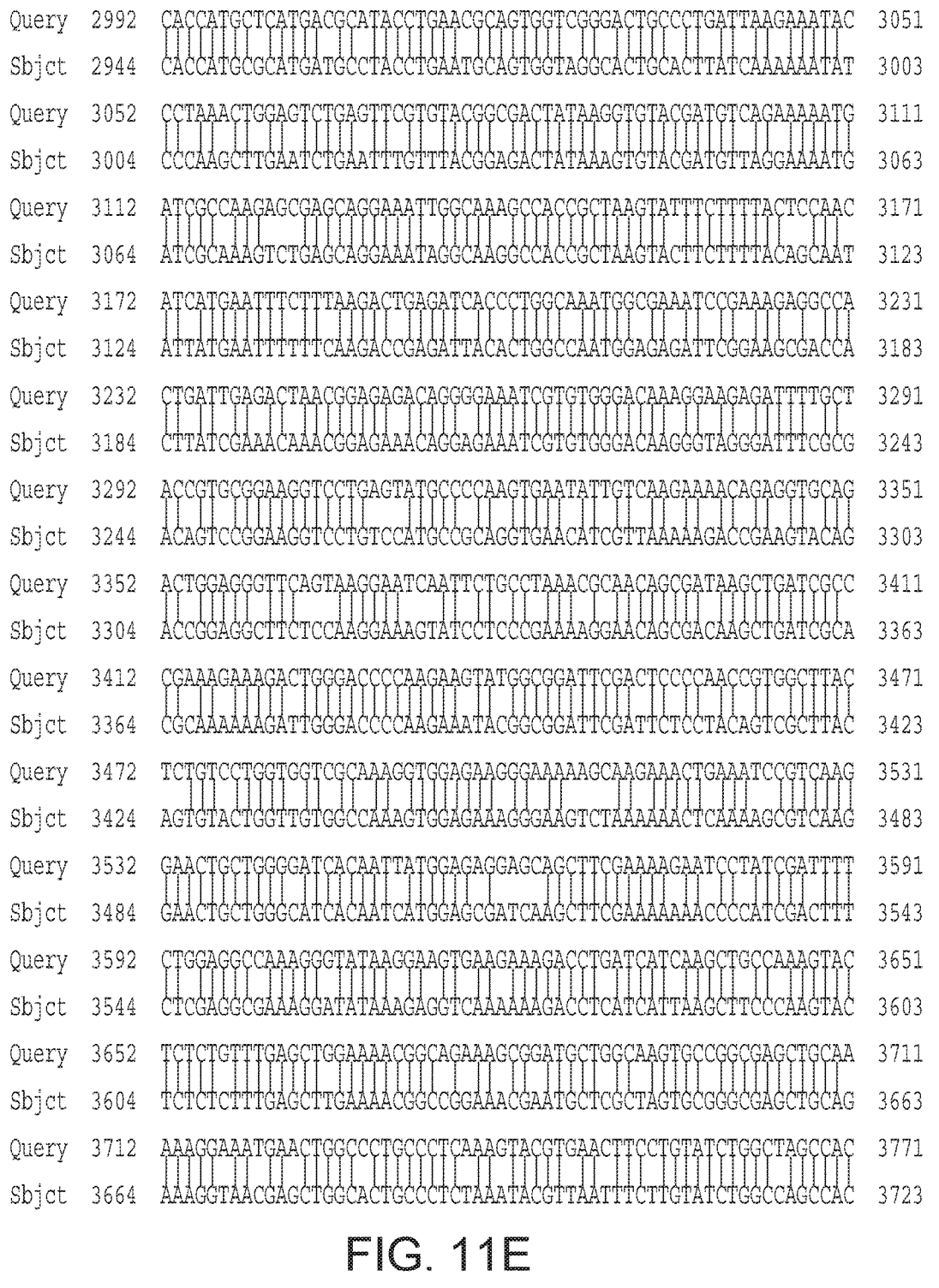

```
Query  2992  CACCATGCTCATGACGCATACCTGAACGCAGTGGTCGGGACTGCCCTGATTAAGAAATAC  3051
Sbjct  2944  CACCATGCGCATGATGCCTACCTGAATGCAGTGGTAGGCACTGCACTTATCAAAAAATAT  3003

Query  3052  CCTAAACTGGAGTCTGAGTTCGTGTACGGCGACTATAAGGTGTACGATGTCAGAAAAATG  3111
Sbjct  3004  CCCAAGCTTGAATCTGAATTTGTTTACGGAGACTATAAAGTGTACGATGTTAGGAAAATG  3063

Query  3112  ATCGCCAAGAGCGAGCAGGAAATTGGCAAAGCCACCGCTAAGTATTTCTTTTACTCCAAC  3171
Sbjct  3064  ATCGCAAAGTCTGAGCAGGAAATAGGCAAGGCCACCGCTAAGTACTTCTTTTACAGCAAT  3123

Query  3172  ATCATGAATTTCTTTAAGACTGAGATCACCCTGGCAAATGGCGAAATCCGAAAGAGGCCA  3231
Sbjct  3124  ATTATGAATTTTTTCAAGACCGAGATTACACTGGCCAATGGAGAGATTCGGAAGCGACCA  3183

Query  3232  CTGATTGAGACTAACGGAGAGACAGGGGAAATCGTGTGGGACAAAGGAAGAGATTTTGCT  3291
Sbjct  3184  CTTATCGAAACAAACGGAGAAACAGGAGAAATCGTGTGGGACAAGGGTAGGGATTTCGCG  3243

Query  3292  ACCGTGCGGAAGGTCCTGAGTATGCCCCAAGTGAATATTGTCAAGAAAACAGAGGTGCAG  3351
Sbjct  3244  ACAGTCCGGAAGGTCCTGTCCATGCCGCAGGTGAACATCGTTAAAAAGACCGAAGTACAG  3303

Query  3352  ACTGGAGGGTTCAGTAAGGAATCAATTCTGCCTAAACGCAACAGCGATAAGCTGATCGCC  3411
Sbjct  3304  ACCGGAGGCTTCTCCAAGGAAAGTATCCTCCCGAAAAGGAACAGCGACAAGCTGATCGCA  3363

Query  3412  CGAAAGAAAGACTGGGACCCCAAGAAGTATGGCGGATTCGACTCCCCAACCGTGGCTTAC  3471
Sbjct  3364  CGCAAAAAAGATTGGGACCCCAAGAAATACGGCGGATTCGATTCTCCTACAGTCGCTTAC  3423

Query  3472  TCTGTCCTGGTGGTCGCAAAGGTGGAGAAGGGAAAAAGCAAGAAACTGAAATCCGTCAAG  3531
Sbjct  3424  AGTGTACTGGTTGTGGCCAAAGTGGAGAAAGGGAAGTCTAAAAAACTCAAAAGCGTCAAG  3483

Query  3532  GAACTGCTGGGGATCACAATTATGGAGAGGAGCAGCTTCGAAAAGAATCCTATCGATTTT  3591
Sbjct  3484  GAACTGCTGGGCATCACAATCATGGAGCGATCAAGCTTCGAAAAAAACCCCATCGACTTT  3543

Query  3592  CTGGAGGCCAAAGGGTATAAGGAAGTGAAGAAAGACCTGATCATCAAGCTGCCAAAGTAC  3651
Sbjct  3544  CTCGAGGCGAAAGGATATAAAGAGGTCAAAAAAGACCTCATCATTAAGCTTCCCAAGTAC  3603

Query  3652  TCTCTGTTTGAGCTGGAAAACGGCAGAAAGCGGATGCTGGCAAGTGCCGGCGAGCTGCAA  3711
Sbjct  3604  TCTCTCTTTGAGCTTGAAAACGGCCGGAAACGAATGCTCGCTAGTGCGGGCGAGCTGCAG  3663

Query  3712  AAAGGAAATGAACTGGCCCTGCCCTCAAAGTACGTGAACTTCCTGTATCTGGCTAGCCAC  3771
Sbjct  3664  AAAGGTAACGAGCTGGCACTGCCCTCTAAATACGTTAATTTCTTGTATCTGGCCAGCCAC  3723
```

FIG. 11E

```
Query  3772  TACGAGAAGCTGAAAGGCTCCCCTGAGGATAACGAACAGAAACAGCTGTTTGTGGAGCAG  3831
Sbjct  3724  TATGAAAAGCTCAAAGGGTCTCCCGAAGATAATGAGCAGAAGCAGCTGTTCGTGGAACAA  3783

Query  3832  CACAAGCATTATCTGGACGAGATCATTGAACAGATTAGCGAGTTCTCCAAACGCGTGATC  3891
Sbjct  3784  CACAAACACTACCTTGATGAGATCATCGAGCAAATAAGCGAATTCTCCAAAAGAGTGATC  3843

Query  3892  CTGGCTGACGCAAATCTGGATAAGGTCCTGTCTGCATACAACAAACACAGGGACAAGCCA  3951
Sbjct  3844  CTCGCCGACGCTAACCTCGATAAGGTGCTTTCTGCTTACAATAAGCACAGGGATAAGCCC  3903

Query  3952  ATCAGAGAGCAGGCCGAAAATATCATTCATCTGTTCACTCTGACCAACCTGGGAGCCCCC  4011
Sbjct  3904  ATCAGGGAGCAGGCAGAAAACATTATCCACTTGTTTACTCTGACCAACTTGGGCGCGCCT  3963

Query  4012  GCAGCCTTCAAGTATTTTGACACTACCATCGATCGCAAACGATACACAAGCACTAAGGAG  4071
Sbjct  3964  GCAGCCTTCAAGTACTTCGACACCACCATAGACAGAAAGCGGTACACCTCTACAAAGGAG  4023

Query  4072  GTGCTGGATGCTACCCTGATCCACCAGAGCATTACTGGGCTGTACGAGACAAGGATCGAC  4131
Sbjct  4024  GTCCTGGACGCCACACTGATTCATCAGTCAATTACGGGGCTCTATGAAACAAGAATCGAC  4083

Query  4132  CTGTCCCAGCTGGGGGGAGACA  4153      (SEQ ID NO: 2)
Sbjct  4084  CTCTCTCAGCTCGGTGGAGACA  4105      (SEQ ID NO: 3)
```

FIG. 11F

```
Query  1    ATGGCTCCCAAGAAGAAGCGAAAGGTGGGCATCCACGGCGTGCCCGCTGCCGACAAAAAG  60
            ||||| || ||||||||||| ||||| || |||||||| || || || |||||||| |||
Sbjct  70   ATGGCCCCAAAGAAGAAGCGGAAGGTCGGTATCCACGGAGTCCCAGCAGCCGACAAGAAG  129

Query  61   TATAGTATCGGACTGGATATTGGCACTAACAGCGTGGGATGGGCCGTCATCACCGACGAG  120
            || || ||||| ||||| || ||||| |||   ||||| ||||||||| ||||||||||||
Sbjct  130  TACAGCATCGGCCTGGACATCGGCACCAACTCTGTGGGCTGGGCCGTGATCACCGACGAG  189

Query  121  TACAAAGTGCCAAGCAAGAAGTTCAAGGTCCTGGGAAACACCGATAGACACAGTATCAAG  180
            ||||| ||||| |||||||| |||||||| ||||| ||||||||  | ||||| ||||||
Sbjct  190  TACAAGGTGCCCAGCAAGAAATTCAAGGTGCTGGGCAACACCGACCGGCACAGCATCAAG  249

Query  181  AAAAATCTGATTGGAGCCCTGCTGTTCGACTCAGGGGAGACAGCTGAAGCAACTAGGCTG  240
            || || ||||| ||||||||||||||||||   || || ||||| || || ||  |||||
Sbjct  250  AAGAACCTGATCGGAGCCCTGCTGTTCGACAGCGGCGAAACAGCCGAGGCCACCCGGCTG  309

Query  241  AAAAGAACAGCTAGGAGACGGTATACTCGCCGAAAGAATCGGATCTGCTACCTCCAGGAG  300
            || ||||| || || || || || ||  | || ||||| ||||||||||| || || |||
Sbjct  310  AAGAGAACCGCCAGAAGAAGATACACCAGACGGAAGAACCGGATCTGCTATCTGCAAGAG  369

Query  301  ATTTTCTCCAACGAAATGGCCAAGGTGGACGATAGTTTCTTTCATCGCCTGGAGGAATCA  360
            || |||  ||||||| ||||||||||||||||| || ||||| ||  | |||||| || || 
Sbjct  370  ATCTTCAGCAACGAGATGGCCAAGGTGGACGACAGCTTCTTCCACAGACTGGAAGAGTCC  429

Query  361  TTCCTGGTCGAGGAAGATAAGAAACACGAGAGGCATCCCATCTTTGGCAACATTGTGGAC  420
            |||||||| || || |||||||| |||||| |||| ||||||||| |||||||| ||||||
Sbjct  430  TTCCTGGTGGAAGAGGATAAGAAGCACGAGCGGCACCCCATCTTCGGCAACATCGTGGAC  489

Query  421  GAGGTCGCTTATCACGAAAAGTACCCTACAATCTATCATCTGCGGAAGAAACTGGTGGAC  480
            ||||| || || ||||| |||||||| || ||||| || ||| | |||||||||||||||
Sbjct  490  GAGGTGGCCTACCACGAGAAGTACCCCACCATCTACCACCTGAGAAAGAAACTGGTGGAC  549

Query  481  AGCACTGATAAGGCAGACCTGCGCCTGATCTATCTGGCCCTGGCTCACATGATTAAGTTC  540
            ||||| || ||||| |||||||| ||||||||||||||||||||| |||||||| ||||||
Sbjct  550  AGCACCGACAAGGCCGACCTGCGGCTGATCTATCTGGCCCTGGCCCACATGATCAAGTTC  609

Query  541  AGGGGGCATTTTCTGATCGAGGGCGATCTGAACCCAGACAATTCCGATGTGGACAAGCTG  600
             |||| || || |||||||||||||| |||||||| ||||   ||| ||||||||||||
Sbjct  610  CGGGGCCACTTCCTGATCGAGGGCGACCTGAACCCCGACAACAGCGACGTGGACAAGCTG  669

Query  601  TTCATCCAGCTGGTCCAGACATACAATCAGCTGTTTGAGGAAAACCCCATTAATGCATCT  660
            |||||||||||||| ||||| ||||| |||||||| |||||||||||||| || ||
Sbjct  670  TTCATCCAGCTGGTGCAGACCTACAACCAGCTGTTCGAGGAAAACCCCATCAACGCCAGC  729

Query  661  GGGGTGGACGCAAAAGCCATCCTGAGTGCCAGACTGTCTAAGAGTAGGAGACTGGAGAAC  720
            || ||||||||| || |||||||||  ||||||||||   ||||| ||  | ||||| ||
Sbjct  730  GGCGTGGACGCCAAGGCCATCCTGTCTGCCAGACTGAGCAAGAGCAGACGGCTGGAAAAT  789
```

FIG. 12A

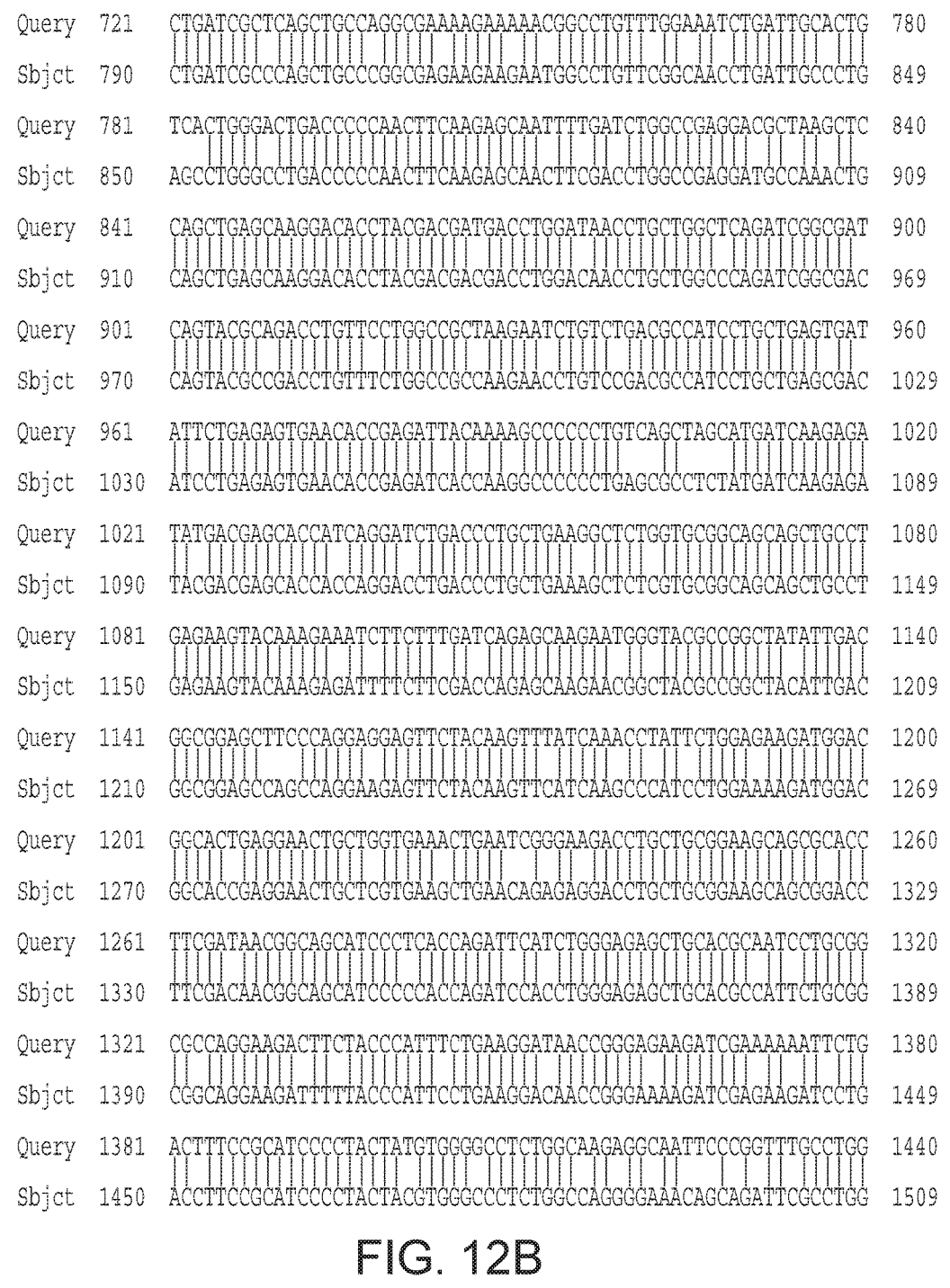

```
Query  721   CTGATCGCTCAGCTGCCAGGCGAAAAGAAAAACGGCCTGTTTGGAAATCTGATTGCACTG  780
Sbjct  790   CTGATCGCCCAGCTGCCCGGCGAGAAGAAGAATGGCCTGTTCGGCAACCTGATTGCCCTG  849

Query  781   TCACTGGGACTGACCCCCAACTTCAAGAGCAATTTTGATCTGGCCGAGGACGCTAAGCTC  840
Sbjct  850   AGCCTGGGCCTGACCCCCAACTTCAAGAGCAACTTCGACCTGGCCGAGGATGCCAAACTG  909

Query  841   CAGCTGAGCAAGGACACCTACGACGATGACCTGGATAACCTGCTGGCTCAGATCGGCGAT  900
Sbjct  910   CAGCTGAGCAAGGACACCTACGACGACGACCTGGACAACCTGCTGGCCCAGATCGGCGAC  969

Query  901   CAGTACGCAGACCTGTTCCTGGCCGCTAAGAATCTGTCTGACGCCATCCTGCTGAGTGAT  960
Sbjct  970   CAGTACGCCGACCTGTTTCTGGCCGCCAAGAACCTGTCCGACGCCATCCTGCTGAGCGAC  1029

Query  961   ATTCTGAGAGTGAACACCGAGATTACAAAAGCCCCCCTGTCAGCTAGCATGATCAAGAGA  1020
Sbjct  1030  ATCCTGAGAGTGAACACCGAGATCACCAAGGCCCCCCTGAGCGCCTCTATGATCAAGAGA  1089

Query  1021  TATGACGAGCACCATCAGGATCTGACCCTGCTGAAGGCTCTGGTGCGGCAGCAGCTGCCT  1080
Sbjct  1090  TACGACGAGCACCACCAGGACCTGACCCTGCTGAAAGCTCTCGTGCGGCAGCAGCTGCCT  1149

Query  1081  GAGAAGTACAAAGAAATCTTCTTTGATCAGAGCAAGAATGGGTACGCCGGCTATATTGAC  1140
Sbjct  1150  GAGAAGTACAAAGAGATTTTCTTCGACCAGAGCAAGAACGGCTACGCCGGCTACATTGAC  1209

Query  1141  GGCGGAGCTTCCCAGGAGGAGTTCTACAAGTTTATCAAACCTATTCTGGAGAAGATGGAC  1200
Sbjct  1210  GGCGGAGCCAGCCAGGAAGAGTTCTACAAGTTCATCAAGCCCATCCTGGAAAAGATGGAC  1269

Query  1201  GGCACTGAGGAACTGCTGGTGAAACTGAATCGGGAAGACCTGCTGCGGAAGCAGCGCACC  1260
Sbjct  1270  GGCACCGAGGAACTGCTCGTGAAGCTGAACAGAGAGGACCTGCTGCGGAAGCAGCGGACC  1329

Query  1261  TTCGATAACGGCAGCATCCCTCACCAGATTCATCTGGGAGAGCTGCACGCAATCCTGCGG  1320
Sbjct  1330  TTCGACAACGGCAGCATCCCCCACCAGATCCACCTGGGAGAGCTGCACGCCATTCTGCGG  1389

Query  1321  CGCCAGGAAGACTTCTACCCATTTCTGAAGGATAACCGGGAGAAGATCGAAAAAATTCTG  1380
Sbjct  1390  CGGCAGGAAGATTTTTACCCATTCCTGAAGGACAACCGGGAAAAGATCGAGAAGATCCTG  1449

Query  1381  ACTTTCCGCATCCCCTACTATGTGGGGCCTCTGGCAAGAGGCAATTCCCGGTTTGCCTGG  1440
Sbjct  1450  ACCTTCCGCATCCCCTACTACGTGGGCCCTCTGGCCAGGGGAAACAGCAGATTCGCCTGG  1509
```

FIG. 12B

```
Query  1441  ATGACCCGCAAGTCTGAGGAAACAATCACTCCCTGGAACTTCGAGGAAGTGGTCGATAAG  1500
             |||||| | |||   |||||||| ||||| ||||||||||||||||||||||| || |||
Sbjct  1510  ATGACCAGAAAGAGCGAGGAAACCATCACCCCCTGGAACTTCGAGGAAGTGGTGGACAAG  1569

Query  1501  GGCGCTTCCGCACAGTCTTTCATTGAGAGGATGACAAATTTTGACAAGAACCTGCCAAAT  1560
             ||||||||||| |||   ||||| ||| ||||||| || || || ||||||||||| || 
Sbjct  1570  GGCGCTTCCGCCCAGAGCTTCATCGAGCGGATGACCAACTTCGATAAGAACCTGCCCAAC  1629

Query  1561  GAAAAAGTGCTGCCCAAGCACAGCCTGCTGTACGAGTATTTCACCGTCTATAACGAACTG  1620
             || || |||||||||||||||||||||||||||||||| |||||||| |||||||| |||
Sbjct  1630  GAGAAGGTGCTGCCCAAGCACAGCCTGCTGTACGAGTACTTCACCGTGTATAACGAGCTG  1689

Query  1621  ACAAAGGTGAAATACGTCACTGAGGGCATGAGAAAGCCTGCCTTCCTGTCCGGAGAACAG  1680
             || || ||||||||||| || ||||| ||||||||||| |||||||||  ||| || |||
Sbjct  1690  ACCAAAGTGAAATACGTGACCGAGGGAATGAGAAAGCCCGCCTTCCTGAGCGGCGAGCAG  1749

Query  1681  AAGAAAGCTATCGTGGACCTGCTGTTTAAAACCAATCGGAAGGTGACAGTCAAGCAGCTG  1740
             || || || ||||||||||||||||| || ||||| ||||| ||||| || |||||||||
Sbjct  1750  AAAAAGGCCATCGTGGACCTGCTGTTCAAGACCAACCGGAAAGTGACCGTGAAGCAGCTG  1809

Query  1741  AAAGAGGACTACTTCAAGAAAATTGAATGTTTCGATTCTGTGGAGATCAGTGGGGTCGAA  1800
             ||||||||||||||||||||||| || || ||||| || ||||| |||   || || |||
Sbjct  1810  AAAGAGGACTACTTCAAGAAAATCGAGTGCTTCGACTCCGTGGAAATCTCCGGCGTGGAA  1869

Query  1801  GACAGGTTTAACGCCTCTCTGGGCACCTACCACGATCTGCTGAAGATCATTAAGGATAAA  1860
             ||  |||| |||||||| |||||||| ||||||||||||||||| || || ||||| || 
Sbjct  1870  GATCGGTTCAACGCCTCCCTGGGCACATACCACGATCTGCTGAAAATTATCAAGGACAAG  1929

Query  1861  GACTTCCTGGACAACGAGGAAAATGAGGACATCCTGGAGGACATTGTGCTGACCCTGACA  1920
             |||||||||||||| |||||||| |||||||| ||||| || || |||||||||||||||
Sbjct  1930  GACTTCCTGGACAATGAGGAAAACGAGGACATTCTGGAAGATATCGTGCTGACCCTGACA  1989

Query  1921  CTGTTTGAGGATCGGGAAATGATCGAGGAACGCCTGAAGACCTACGCCCATCTGTTCGAT  1980
             |||||||||||  | || |||||||||||||| ||||| ||||| ||||| |||||||| 
Sbjct  1990  CTGTTTGAGGACAGAGAGATGATCGAGGAACGGCTGAAAACCTATGCCCACCTGTTCGAC  2049

Query  1981  GACAAAGTGATGAAACAGCTGAAGCGAAGGAGATACACTGGGTGGGGCCGACTGAGCAGG  2040
             |||||||||||||| |||||||||||  |||||||||| || |||||| | |||||| ||
Sbjct  2050  GACAAAGTGATGAAGCAGCTGAAGCGGCGGAGATACACCGGCTGGGGCAGGCTGAGCCGG  2109

Query  2041  AAGCTGATCAATGGCATTCGCGACAAACAGAGTGGAAAGACAATCCTGGACTTTCTGAAG  2100
             ||||||||||| ||||| || ||||| |||   || |||||||||||||| || ||||||
Sbjct  2110  AAGCTGATCAACGGCATCCGGGACAAGCAGTCCGGCAAGACAATCCTGGATTTCCTGAAG  2169

Query  2101  TCAGATGGCTTCGCTAACAGGAATTTTATGCAGCTGATTCACGATGACTCTCTGACTTTC  2160
             || || |||||||| ||||| || || ||||||||||| ||||| |||   ||||| || 
Sbjct  2170  TCCGACGGCTTCGCCAACAGAAACTTCATGCAGCTGATCCACGACGACAGCCTGACCTTT  2229
```

FIG. 12C

```
Query  2161  AAAGAGGACATCCAGAAGGCACAGGTGTCCGGACAGGGGGACTCTCTGCACGAGCATATC  2220

Sbjct  2230  AAAGAGGACATCCAGAAAGCCCAGGTGTCCGGCCAGGGCGATAGCCTGCACGAGCACATT  2289

Query  2221  GCAAACCTGGCCGGGAGCCCTGCCATCAAGAAAGGCATCCTCCAGACCGTGAAGGTGGTG  2280

Sbjct  2290  GCCAATCTGGCCGGCAGCCCCGCCATTAAGAAGGGCATCCTGCAGACAGTGAAGGTGGTG  2349

Query  2281  GACGAGCTGGTGAAAGTCATGGGAAGACATAAGCCAGAAAACATCGTGATTGAGATGGCC  2340

Sbjct  2350  GACGAGCTCGTGAAAGTGATGGGCCGGCACAAGCCCGAGAACATCGTGATCGAAATGGCC  2409

Query  2341  AGGGAGAATCAGACCACACAGAAAGGGCAGAAGAACTCTCGGGAGCGCATGAAACGCATC  2400

Sbjct  2410  AGAGAGAACCAGACCACCCAGAAGGGACAGAAGAACAGCCGCGAGAGAATGAAGCGGATC  2469

Query  2401  GAGGAAGGAATTAAGGAACTGGGGAGTCAGATCCTGAAAGAGCACCCCGTGGAAAACACA  2460

Sbjct  2470  GAAGAGGGCATCAAAGAGCTGGGCAGCCAGATCCTGAAAGAACACCCCGTGGAAAACACC  2529

Query  2461  CAGCTCCAGAATGAGAAGCTGTATCTGTACTACCTCCAGAATGGCCGCGATATGTACGTG  2520

Sbjct  2530  CAGCTGCAGAACGAGAAGCTGTACCTGTACTACCTGCAGAATGGGCGGGATATGTACGTG  2589

Query  2521  GACCAGGAGCTGGATATTAACCGACTGTCAGATTATGACGTGGATCATATCGTCCCACAG  2580

Sbjct  2590  GACCAGGAACTGGACATCAACCGGCTGTCCGACTACGATGTGGACCATATCGTGCCTCAG  2649

Query  2581  TCATTCCTGAAAGATGACAGCATTGACAATAAGGTGCTGACCCGCAGCGACAAAAACCGA  2640

Sbjct  2650  AGCTTTCTGAAGGACGACTCCATCGACAACAAGGTGCTGACCAGAAGCGACAAGAACCGG  2709

Query  2641  GGAAAGAGTGATAATGTCCCCTCAGAGGAAGTGGTCAAGAAAATGAAGAACTACTGGAGG  2700

Sbjct  2710  GGCAAGAGCGACAACGTGCCCTCCGAAGAGGTCGTGAAGAAGATGAAGAACTACTGGCGG  2769

Query  2701  CAGCTGCTGAATGCCAAACTGATCACCCAGCGAAAGTTTGATAACCTGACAAAAGCTGAG  2760

Sbjct  2770  CAGCTGCTGAACGCCAAGCTGATTACCCAGAGAAAGTTCGACAATCTGACCAAGGCCGAG  2829

Query  2761  AggggggggCCTGTCCGAACTGGACAAAGCAGGCTTCATCAAGCGACAGCTGGTGGAGACA  2820

Sbjct  2830  AGAGGCGGCCTGAGCGAACTGGATAAGGCCGGCTTCATCAAGAGACAGCTGGTGGAAACC  2889

Query  2821  AGGCAGATCACAAAGCACGTCGCTCAGATCCTGGACAGCAGGATGAACACCAAGTACGAT  2880

Sbjct  2890  CGGCAGATCACAAAGCACGTGGCACAGATCCTGGACTCCCGGATGAACACTAAGTACGAC  2949
```

FIG. 12D

```
Query  2881  GAGAATGACAAACTGATCCGGGAAGTGAAGGTCATTACACTGAAGTCAAAACTGGTGAGC  2940
Sbjct  2950  GAGAATGACAAGCTGATCCGGGAAGTGAAAGTGATCACCCTGAAGTCCAAGCTGGTGTCC  3009

Query  2941  GACTTTAGGAAAGATTTCCAGTTCTACAAGGTCAGAGAGATCAACAACTACCACCATGCT  3000
Sbjct  3010  GATTTCCGGAAGGATTTCCAGTTTTACAAAGTGCGCGAGATCAACAACTACCACCACGCC  3069

Query  3001  CATGACGCATACCTGAACGCAGTGGTCGGGACTGCCCTGATTAAGAAATACCCTAAACTG  3060
Sbjct  3070  CACGACGCCTACCTGAACGCCGTCGTGGGAACCGCCCTGATCAAAAAGTACCCTAAGCTG  3129

Query  3061  GAGTCTGAGTTCGTGTACGGCGACTATAAGGTGTACGATGTCAGAAAAATGATCGCCAAG  3120
Sbjct  3130  GAAAGCGAGTTCGTGTACGGCGACTACAAGGTGTACGACGTGCGGAAGATGATCGCCAAG  3189

Query  3121  AGCGAGCAGGAAATTGGCAAAGCCACCGCTAAGTATTTCTTTTACTCCAACATCATGAAT  3180
Sbjct  3190  AGCGAGCAGGAAATCGGCAAGGCTACCGCCAAGTACTTCTTCTACAGCAACATCATGAAC  3249

Query  3181  TTCTTTAAGACTGAGATCACCCTGGCAAATGGCGAAATCCGAAAGAGGCCACTGATTGAG  3240
Sbjct  3250  TTTTTCAAGACCGAGATTACCCTGGCCAACGGCGAGATCCGGAAGCGGCCTCTGATCEAG  3309

Query  3241  ACTAACGGAGAGACAGGGGAAATCGTGTGGGACAAAGGAAGAGATTTTGCTACCGTGCGG  3300
Sbjct  3310  ACAAACGGCGAAACCGGGGAGATCGTGTGGGATAAGGGCCGGGATTTTGCCACCGTGCGG  3369

Query  3301  AAGGTCCTGAGTATGCCCCAAGTGAATATTGTCAAGAAAACAGAGGTGCAGACTGGAGGG  3360
Sbjct  3370  AAAGTGCTGAGCATGCCCCAAGTGAATATCGTGAAAAAGACCGAGGTGCAGACAGGCGGC  3429

Query  3361  TTCAGTAAGGAATCAATTCTGCCTAAACGCAACAGCGATAAGCTGATCGCCCGAAAGAAA  3420
Sbjct  3430  TTCAGCAAAGAGTCTATCCTGCCCAAGAGGAACAGCGATAAGCTGATCGCCAGAAAGAAG  3489

Query  3421  GACTGGGACCCCAAGAAGTATGGCGGATTCGACTCCCCAACCGTGGCTTACTCTGTCCTG  3480
Sbjct  3490  GACTGGGACCCTAAGAAGTACGGCGGCTTCGACAGCCCCACCGTGGCCTATTCTGTGCTG  3549

Query  3481  GTGGTCGCAAAGGTGGAGAAGGGAAAAAGCAAGAAACTGAAATCCGTCAAGGAACTGCTG  3540
Sbjct  3550  GTGGTGGCCAAAGTGGAAAAGGGCAAGTCCAAGAAACTGAAGAGTGTGAAAGAGCTGCTG  3609

Query  3541  GGGATCACAATTATGGAGAGGAGCAGCTTCGAAAAGAATCCTATCGATTTTCTGGAGGCC  3600
Sbjct  3610  GGGATCACCATCATGGAAAGAAGCAGCTTCGAGAAGAATCCCATCGACTTTCTGGAAGCC  3669
```

FIG. 12E

```
Query  3601  AAAGGGTATAAGGAAGTGAAGAAAGACCTGATCATCAAGCTGCCAAAGTACTCTCTGTTT  3660

Sbjct  3670  AAGGGCTACAAAGAAGTGAAAAAGGACCTGATCATCAAGCTGCCTAAGTACTCCCTGTTC  3729

Query  3661  GAGCTGGAAAACGGCAGAAAGCGGATGCTGGCAAGTGCCGGCGAGCTGCAAAAAGGAAAT  3720

Sbjct  3730  GAGCTGGAAAACGGCCGGAAGAGAATGCTGGCCTCTGCCGGCGAACTGCAGAAGGGAAAC  3789

Query  3721  GAACTGGCCCTGCCCTCAAAGTACGTGAACTTCCTGTATCTGGCTAGCCACTACGAGAAG  3780

Sbjct  3790  GAACTGGCCCTGCCCTCCAAATATGTGAACTTCCTGTACCTGGCCAGCCACTATGAGAAG  3849

Query  3781  CTGAAAGGCTCCCCTGAGGATAACGAACAGAAACAGCTGTTTGTGGAGCAGCACAAGCAT  3840

Sbjct  3850  CTGAAGGGCTCCCCCGAGGATAATGAGCAGAAACAGCTGTTTGTGGAACAGCACAAGCAC  3909

Query  3841  TATCTGGACGAGATCATTGAACAGATTAGCGAGTTCTCCAAACGCGTGATCCTGGCTGAC  3900

Sbjct  3910  TACCTGGACGAGATCATCGAGCAGATCAGCGAGTTCTCCAAGAGAGTGATCCTGGCCGAC  3969

Query  3901  GCAAATCTGGATAAGGTCCTGTCTGCATACAACAAACACAGGGACAAGCCAATCAGAGAG  3960

Sbjct  3970  GCTAATCTGGACAAAGTGCTGTCCGCCTACAACAAGCACCGGGATAAGCCCATCAGAGAG  4029

Query  3961  CAGGCCGAAAATATCATTCATCTGTTCACTCTGACCAACCTGGGAGCCCCCGCAGCCTTC  4020

Sbjct  4030  CAGGCCGAGAATATCATCCACCTGTTTACCCTGACCAATCTGGGAGCCCCTGCCGCCTTC  4089

Query  4021  AAGTATTTTGACACTACCATCGATCGCAAACGATACACAAGCACTAAGGAGGTGCTGGAT  4080

Sbjct  4090  AAGTACTTTGACACCACCATCGACCGGAAGAGGTACACCAGCACCAAAGAGGTGCTGGAC  4149

Query  4081  GCTACCCTGATCCACCAGAGCATTACTGGGCTGTACGAGACAAGGATCGACCTGTCCCAG  4140

Sbjct  4150  GCCACCCTGATCCACCAGAGCATCACCGGCCTGTACGAGACACGGATCGACCTGTCTCAG  4209

Query  4141  CTGGGGGGAGACAAACGCCCAGCCGCCACCAAGAAAGCAGGACAGGCAAAGAAGAAGAAG  4200

Sbjct  4210  CTGGGAGGCGACAAGCGTCCTGCTGCTACTAAGAAAGCTGGTCAAGCTAAGAAAAAGAAA  4269

Query  4201  TGA  4203      (SEQ ID NO: 4)

Sbjct  4270  TGA  4272      (SEQ ID NO: 5)
```

FIG. 12F

COMPOSITIONS AND METHODS DIRECTED TO CRISPR/CAS GENOMIC ENGINEERING SYSTEMS

CROSS-REFERENCE TO RELATED APPLICATIONS

This application is a continuation of pending U.S. application Ser. No. 14/211,858, filed on Mar. 14, 2014, which claims priority to and benefit of U.S. Provisional Application Ser. No. 61/799,586, filed on Mar. 15, 2013, each of which are herein incorporated by reference in their entirety.

FIELD OF THE INVENTION

The invention relates generally to systems for targeted genomic modification in mammalian cells.

SEQUENCE LISTING

The instant application contains a Sequence Listing which has been previously submitted electronically in ASCII format and is hereby incorporated by reference in its entirety. Said ASCII copy, created on May 8, 2014, is named 1458.03NPR_SL.txt and is 31,454 bytes in size, and is made of record in U.S. application Ser. No. 14/211,858, filed on Mar. 14, 2014.

BACKGROUND OF THE INVENTION

Small RNA-based defense systems that provide adaptive, heritable immunity against viruses, plasmids, and other mobile genetic elements have recently been discovered in archaea and bacteria. The RNA and protein components of these immune systems arise from the CRISPR (clustered regularly interspaced short palindromic repeat) and Cas (CRISPR-associated) genes, respectively. CRISPR locus consists of variable similar sized, short regions (spacers) that separate each of short repeats. The spacers are mainly homologous to the invading sequences and the repeats are identical sequences. Cas genes are often located adjacent to the CRISPR locus. Prokaryotes with CRISPR-Cas immune systems capture short invader sequences with the CRISPR loci in the genomes, and small RNAs produced from the CRISPR loci (crRNAs) guide Cas proteins to recognize and degrade (or otherwise silence) the invading nucleic acids.

CRISPR-Cas systems operate through three general steps to provide immunity: adaptation, crRNA biogenesis, and invader silencing. In the adaptation phase, a short fragment of foreign DNA (protospacer) is acquired from the invader and integrated into the host CRISPR locus adjacent to the leader. Protospacer adjacent motifs (PAMs) are found near invader sequences selected for CRISPR integration.

In the crRNA biogenesis phase, CRISPR locus transcripts are processed to release a set of small individual mature crRNAs (each targeting a different sequence). Mature crRNA generally retain some of the repeat sequence, which is thought to provide a recognizable signature of the crRNA. In the silencing phase, crRNA-Cas protein complexes recognize and degrade foreign DNAs or RNAs.

There are three types of CRISP-Cas systems. Type II CRISPR-Cas systems has been extensively studied partially because they offered practical applications in the dairy industry to generate phage-resistant *Streptococcus thermophilus* (*S. thermophilus*) strains. In addition to its content and architecture, Type II systems also differ from other types in the biogenesis of crRNA. A set of small non-coding RNAs called tracrRNA (trans-activating CRISPR RNA) are produced from a region outside but close to the CRISPR locus. The tracrRNAs are partially complementary to the type II CRISPR repeat sequences and hybridize to the repeats within the long precursor CRISPR RNA and the RNA duplexes are processed by non-CRISPR RNase III to generate mature crRNAs. Cas9, a large type II signature protein, is thought to be the only protein involved in the crRNA-guided silencing of foreign nucleic acids.

Jinek et al. "A Programmable Dual-RNA—Guided DNA Endonuclease in Adaptive Bacterial Immunity," *Science* 337(6096), p.816-821 (August 2012) show that crRNA fused to a tracrRNA (called crRNA-tracrRNA chimera or guide chimeric RNAs) is sufficient to direct Cas9 protein to sequence-specifically cleave target DNA sequences matching the crRNA using in vitro reconstitution of *Streptococcus pyogenes* (*S. pyogenes*) type II CRISPR system. However, the study was based on biochemical assays and did not show whether or not the Cas9-crRNA-tracrRNA system would work in the cells of eukaryotic organisms.

To explore the potential of RNA-programmed Cas9 for genome-editing applications in mammalian cells, Mali et al., "RNA-Guided Human Genome Engineering via Cas9" *Science Express* (Jan. 3, 2013) and Cong et al., "Multiplex Genome Engineering Using CRISPR/Cas Systems" *Science Express* (Jan. 3, 2013) independently engineer Cas9 and RNA components of the bacterial type II CRISPR system in human cells and/or mouse cells. Both labs were able to introduce precise double stranded break at endogenous genomic loci in human cells and/or mouse cells using human codon-optimized version of the *S. pyogenes* Cas9 proteins directed by short RNAs. The two labs designed and used different nucleic acid sequences to encode codon-optimized *S. pyogenes* Cas9 protein.

RNA-guided genome targeting defines a potential new class of genome engineering tools. What is needed in the art are efficient and versatile methods and tools for RNA-programmed genome engineering. Improved efficient systems using RNA-programmed Cas9 can be used, for example, to study biology by perturbing gene networks, and also for example, can be used to treat genetic diseases by repairing genetic defects or by reintroducing genes into cells.

SUMMARY OF THE INVENTION

The present disclosure provides an all-in-one CRISPR II system for genomic modification comprising (i) an polynucleotide encoding the *S. pyogenes* Cas9 protein, and (ii) guide-RNAs for RNA-guided genome engineering in human or mouse cells. The present specification describes the design, expression and testing of a polynucleotide that has been optimized for expression of *S. pyogenes* Cas9 protein in mammalian cells such as human or mouse cells, and describes the testing of the all-in-one system for RNA-guided genome engineering in human cells. The disclosure further provides human codon-optimized polynucleotides encoding a *S. pyogenes* Cas9 protein where the protein also bears an N terminal myc-tag and two nuclear localization signals (NLS), located in the N-terminus and C-terminus, respectively.

BRIEF DESCRIPTION OF THE DRAWINGS

FIG. 3A provides a schematic of the expression construct EF1-hspCas9-H1-AAVS. FIG. 3B provides a schematic of an expression construct EF1-spCas9-mcherry-H1-AAVS. FIG. 3C provides the nucleotide sequence of the AAVS target sequence (SEQ ID NO: 11).

FIG. 6A provides a schematic of an expression construct EF1-hspCas9-H1-Luc. FIG. 6B provides the nucleotide sequences of two gRNAs that target the luciferase sequence. FIG. 6C provides a schematic of homologous recombination event that takes place in a luciferase stable reporter cell line.

FIGS. 10A-10C provide the nucleotide sequence (SEQ ID NO: 1) of the human codon-optimized polynucleotide encoding the *S. pyogenes* Cas9 protein (hspCas9) further comprising an N-terminal myc-tag and two nuclear localization singals.

FIGS. 11A-11F provide a nucleotide sequence alignment of the polynucleotides of two cas9 sequences, where the query sequence is the hspCas9 domain of the present invention, containing only the Cas9 coding region, without sequences encoding the myc-tag or NLS, i.e., the query sequence is nucleotide positions 91 through 4191 of the nucleotide sequence provided in FIG. 10A-10C and SEQ ID NO: 2. The subject sequence is a cas9 sequence of Mali et al., "RNA-Guided Human Genome Engineering via Cas9," Science Express (Jan. 3, 2013); SEQ ID NO: 3.

FIGS. 12A-12F provide a nucleotide sequence alignment of the polynucleotides of two cas9 sequences, where the query sequence is the hspCas9 domain containing the N-terminal and C-terminal NLS, and without sequences encoding the myc-tag, i.e., the query sequence is nucleotide positions 40 through 4242 of the nucleotide sequence provided in FIGS. 10A-10C and SEQ ID NO: 4. The subject sequence is a cas9 sequence of Cong et al., "Multiplex Genome Engineering Using CRISPR/Cas Systems," *Science Express* (Jan. 3, 2013); SEQ ID NO: 5.

DETAILED DESCRIPTION OF THE INVENTION

Figure 1A:
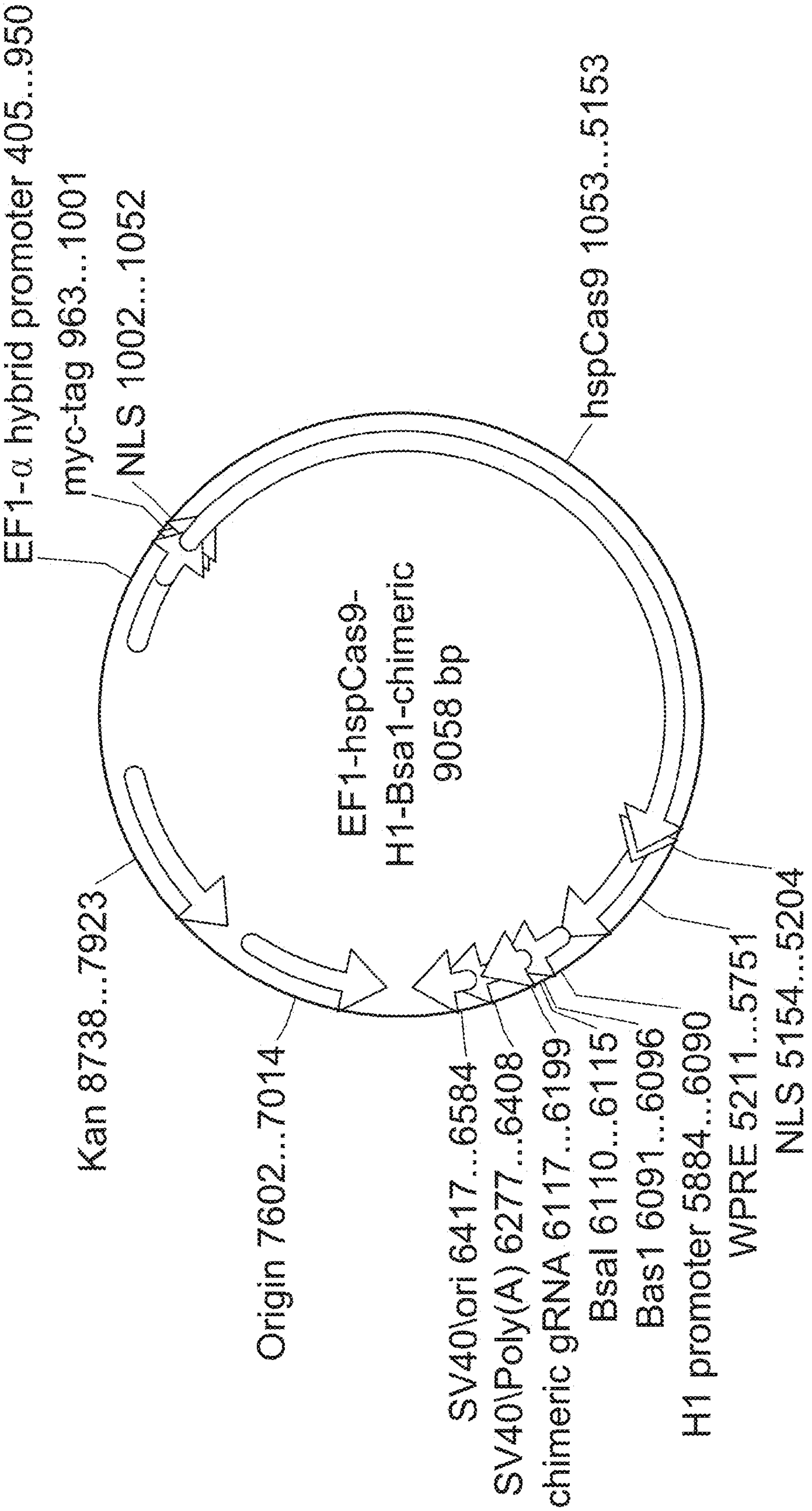
FIG. 1A provides a map of the mammalian expression construct for use with the all-in-one CRISPRII system.

In one aspect, the present disclosure provides a human codon-optimized polynucleotide encoding the *S. pyogenes* Cas9 protein bearing an N terminus Myc tag and two nuclear localization signals (NLS), located in the N terminus and C terminus, respectively. The disclosure also provides all-in-one CRISPR II systems with prokaryote encoded Cas9 that is also able achieve genomic editing in mammalian cells.

Taken together, the present disclosure demonstrates that an engineered all-in-one CRISPR II system is able to achieve genomic targeting and modification in a simple, flexible and highly efficient way. Combination of two or more all-in-one CRISPR II systems with different gRNAs would also allow effective multiplex genome editing.

The all-in-one CRISPR II system has a wide variety of potential applications across basic sciences, biotechnology and biomedicine.

To accommodate the wide variety of potential applications, several features of all-in-one CRISPR II system are customizable. Although the EF1-α hybrid promoter is utilized herein to drive the expression of Cas9 in the all-in-one CRISPR II systems, the design of all-in-one constructs allows easy swapping of the EF1-α hybrid promoter with any kind of pol II promoter. This feature allows all-in-one CRISPR systems to be easily adopted by researchers in different fields. The all-in-one systems described herein also simplify the cloning of gRNA by simply annealing oligos without PCR, and the transformation efficiency of this system achieves 99%. This allows the systems to be easily and cost effectively used by researchers without molecular cloning experience.

EXAMPLES

The following examples are offered to illustrate, but not limit, the claimed invention.

Example 1

Synthesis of a Human Codon-Optimized Polynucleotide Encoding the Cas9 Protein A wide variety of factors regulate and influence gene expression levels. Taking into consideration as many of these factors as possible, a polynucleotide was designed for the highest possible level of expression of Cas9 protein in both human and mouse cells. Parameters used in codon optimization included:

a) codon usage bias,
b) GC content,
c) CpG dinucleotide content,
d) mRNA secondary structure,
e) cryptic mRNA splicing sites,
f) premature PolyA sites,
g) internal chi sites and ribosomal bonding sites,
h) negative CpG islands,
i) RNA instability motif,
j) direct repeats, reverse repeats, and Dyad repeats,
k) restriction sites that may interfere with downstream applications (e.g., cloning),
l) efficiency of translational termination.

The native *S. pyogenes* Cas9 gene employs tandem rare codons that can reduce the efficiency of translation or even disengage the translational machinery. In this case, the codon usage bias was increased by upgrading the codon adaptation index (CAI) to 0.88 in human and in mouse. The GC content was adjusted to 49.93% and unfavorable peaks have been optimized to prolong the half-life of the mRNA. The stem-loop structures, which impact ribosomal binding and stability of mRNA, were broken. In addition, the optimization process modified those negative cis-acting sites and avoided 15 of the most common restriction enzymes, as well as a Bsal site, as listed below.

```
Splice (GGTAAG)

Splice (GGTGAT)

PolyA (AATAAA)

PolyA (ATTAAA)

Destabilizing (ATTTA)

PolyT (TTTTTT)

PolyA (AAAAAAA)

BamHI (GGATCC)

BglII (AGATCT)

EcoRI (GAATTC)

EcoRV (GATATC)

HindIII (AAGCTT)

KpnI (GGTACC)

NcoI (CCATGG)

NdeI (CATATG)

NotI (GCGGCCGC)

PstI (CTGCAG)

SmaI (CCCGGG)

SacI (GAGCTC)

SalI (GTCGAC)

XbaI (TCTAGA)

XhoI (CTCGAG)
```

Based on these optimization criteria, a human codon-optimized polynucleotide encoding the *S. pyogenes* Cas9 protein was generated. See, and SEQ ID NO: 1 nucleotide positions 91through 4191. In addition, the human codon-optimized polynucleotide encoding the *S. pyogenes* Cas9protein was further manipulated by the addition of an N terminal myc-tag (see FIGS. 10A-10C and SEQ ID NO: 1 at nucleotide positions 1 through 39) and by the addition of two nuclear localization signals (NLS), located in the N terminus and C terminus, respectively (see FIGS. 10A-10C and SEQ ID NO: 1 at nucleotide positions 40 through 90, and nucleotide positions 4192 through 4242). This human codon optimized polynucleotide encoding the spCas9 modified by the addition of the N-terminal myc-tag and two NLS (located at the N-terminus and C-terminus) is referred to as hspCas9.

Example 2

Construction of an All-in-One CRISPRII System

In order to achieve high efficiency cleavage of target sequences of interest by Cas9, an all-in-one CRISPRII system was constructed by cloning the human codon optimized Cas9 sequence (hspCas9; SEQ ID NO: 1) and the crRNA-tracrRNA chimeric guide transcripts (see FIG. 1B, gRNA scaffold sequence in lowercase) into a single mammalian expression construct. The single construct engineered for use in this system is depicted in the map shown in FIG. 1A.

As shown in FIG. 1A, expression of the human codon optimized polynucleotide encoding the spCas9 (hspCas9) is driven by the EF1-α hybrid promoter.

To avoid reconstituting the RNA processing machinery, the crRNA-tracrRNA chimeric transcript (referred to as chimeric gRNA) can be easily cloned at the Bsa1 site with 20 base pairs of crRNA target upstream of PAM (protospacer-adjacent motif). See FIG. 1B. Expression of this chimeric gRNA sequence is driven by an upstream H1 polymerase III promoter (see FIG. 1B, H1 promoter is boxed) followed by a woodchuck hepatitis virus post-transcriptional regulatory element (WPRE) sequence to increase protein stability. The H1 promoter has no constraints on the transcription initiation site, unlike the U6 promoter which requires transcription to be initiated with a G.

Figure 1B:
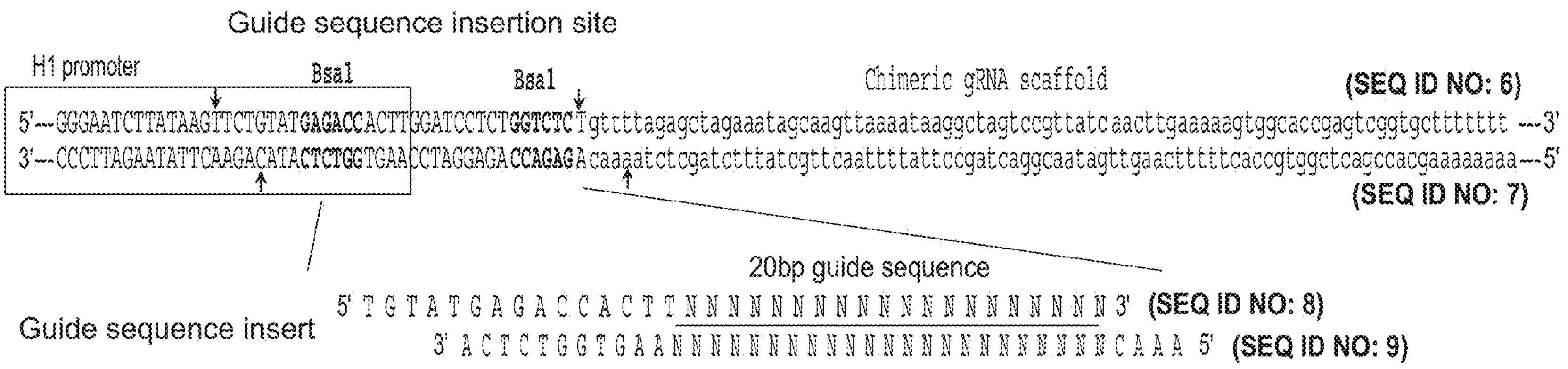
FIG. 1B provides nucleotide sequences and other information describing the guide sequence insertion site in the all-in-one CRISPRII system expression construct.
Figure 1C:
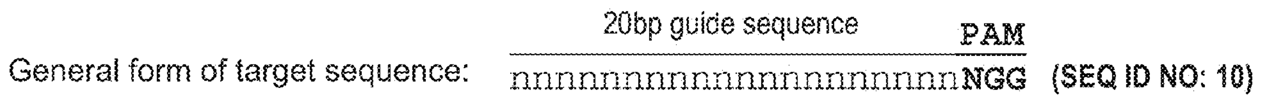
FIG. 1C provides the general form of the target guide sequence to be used in the all-in-one CRISPR II system expression construct.

FIG. 1B provides the structure of the guide sequence insertion site comprising two Bsa1 restriction sites. In order to target a given sequence, the construct can be digested by Bsa1 and a pair of annealed oligonucleotides can be cloned into the all-in-one construct. The target sequence is 20 base pairs in length (FIG. 1C, lowercase) and must be flanked on the 3' end by the NGG PAM sequence (FIG. 1C). This highly flexible approach can target any genomic site in the form of $N_{20}$NGG (SEQ ID NO: 10).

Example 3

Expression of Prokaryote-Encoded Cas9 in Human Cells

Although the all-in-one system described in EXAMPLE 2 used the engineered humanized hspCas9 polynucleotide sequence to express Cas9, the prokaryote *Streptococcus pyogenes* coded cas9 (referred to as spCas9) was also tested for the ability to express in mammalian cell lines.

Figure 2A:
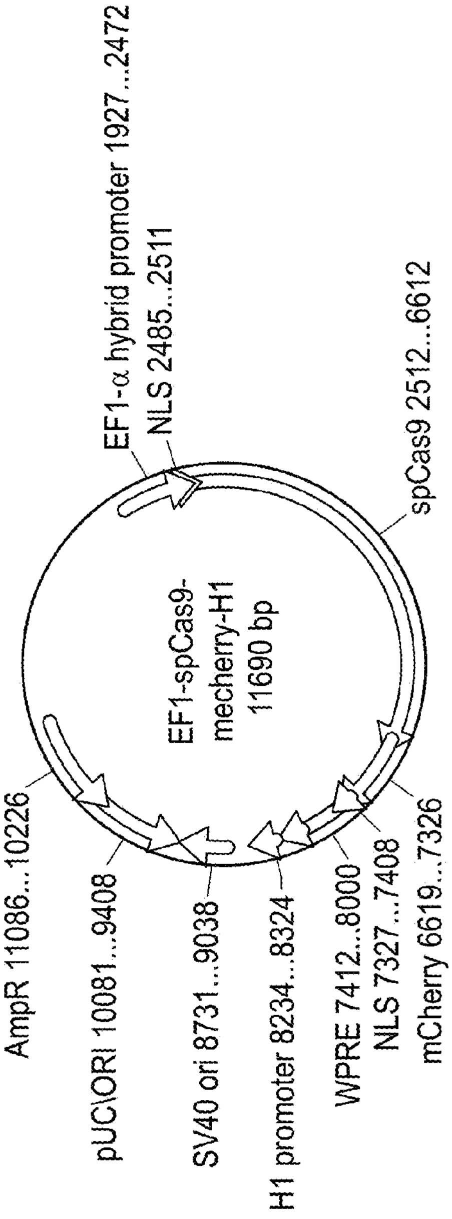
FIG. 2A provides a construct map of an expression vector containing the prokaryote encoded spCas9.

For this purpose, an expression vector containing the prokaryote encoded spCas9 was constructed, as shown in FIG. 2A. As shown in that figure, the spCas9 was augmented with N-terminus and C-terminus NLS, and further fused at the C-terminus with mcherry (red fluorescent protein), thereby allowing the monitoring of expression of spCas9 as well as cellular localization of the protein. Expression of the prokaryote encoded spCas9 was driven by the EF1-α hybrid promoter.

Figure 2B:
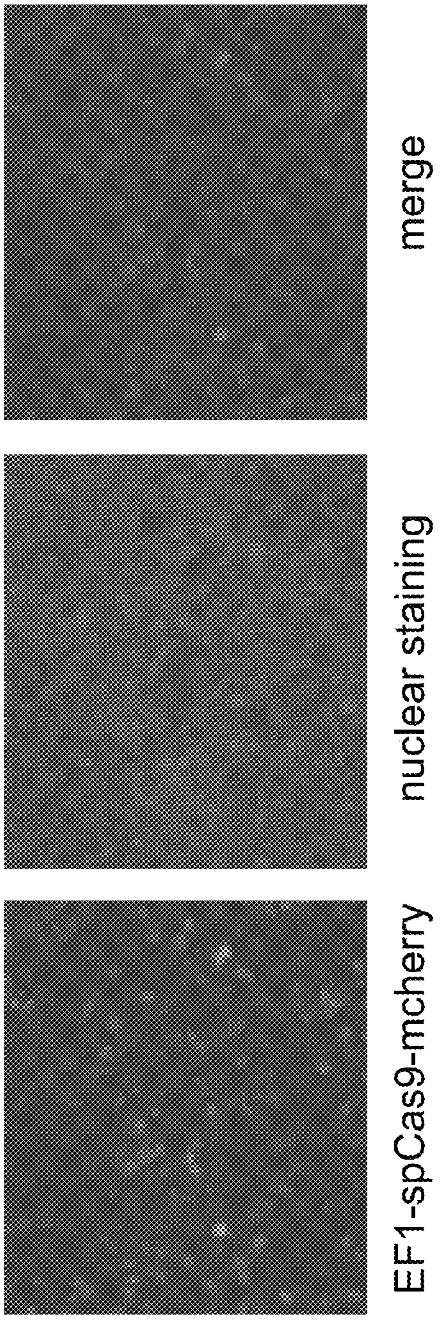
FIG. 2B provides images of human 293T cells containing the expression construct EF1-spCas9-mcherry.

Expression of this construct, termed EF1-spCas9-mcherry, in human 293T cells revealed that prokaryote encoded SpCas9 specifically express well in the nucleus of the human cells (FIG. 2B).

Example 4

Comparison of Homologous Recombination Efficiencies of CRISPRII and TALEN Genomic Targeting Systems Using a GFP Reporter To test the efficiency of stimulating genomic homologous recombination (HR) and target-sequence cleavage with the all-in-one CRISPRII system (using either hspCas9 or prokaryote spCas9 sequence), a chimeric gRNA that targets the adeno-associated virus integration site 1 (AAVS1) fragment was cloned into the all-in-one system vector, and compared its activity to that of a TAL effector nuclease heterodimer (TALEN) targeting the same region (that system termed pZT-AAVS1-TALEN).

The pZT-AAVS1-TALEN system is the most efficient TALEN pair targeting the AAVS1 fragment, as reported by others. That TALEN system shows a 25% target cleavage rate and a 8.1% HR rate in 293T cells.

Figure 3D:
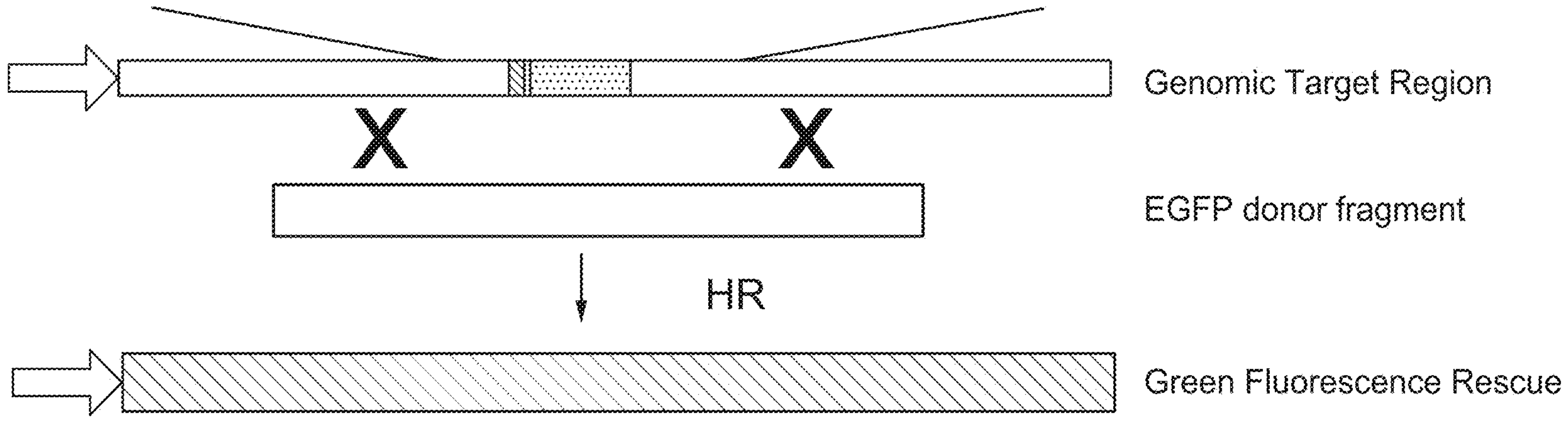
FIG. 3D provides a schematic of the synthetic nucleotide sequences and homologous recombination event in the EGIP reporter cell line.

To conduct the comparison studies, a reporter cell line termed EGIP (enhanced green fluorescent inhibited protein) was genomically engineered, as shown in FIG. 3D. This cell line contains an EGFP sequence (lowercase) bearing a stop codon (taa, double underlined) in the middle of that EGFP sequence). That stop codon is followed by a 53 base pair genomic fragment from the AAVS1 locus (uppercase nucleotides in FIG. 3D). As a result, this cell line does not express GFP. In the presence of an EGFP donor sequence, the GFP signal can hypothetically be restored by homologous recombination (HR), as illustrated in FIG. 3D. The reappearance of GFP positive signal is a marker for the cleavage and homologous recombination event in the cells. Thus, when AAVS sequence is targeted by either TALEN or Cas9, and in the presence of homologous EGFP sequence, the cell line will turn GFP positive.

In the comparison studies, pZT-AAVS1-TALEN was used as a positive control. Two different all-in-one CRISPR II systems targeting the AAVS1 locus were tested. The AAVS target sequence used in these systems is shown in FIG. 3C, and further, the location of that targeted sequence within the AAVS locus is underlined in FIG. 3D. The two CRISPR II systems tested were the human codon optimized all-in-one CRISPR II system (hspCas9 plus AAVS1 gRNA; construct EF1-hspCas9-H1-AAVS; FIG. 3A) and the prokaryote encoded all-in-one CRISPR II system (spCas9 with AAVS1 gRNA; construct EF1-spCas9-mcherry-H1-AAVS; FIG. 3B). Each of these plasmids, including the pZT-AAVS1-TALEN system, both with or without donor fragment, were transfected into EGIP 293T cells.

Figure 4:
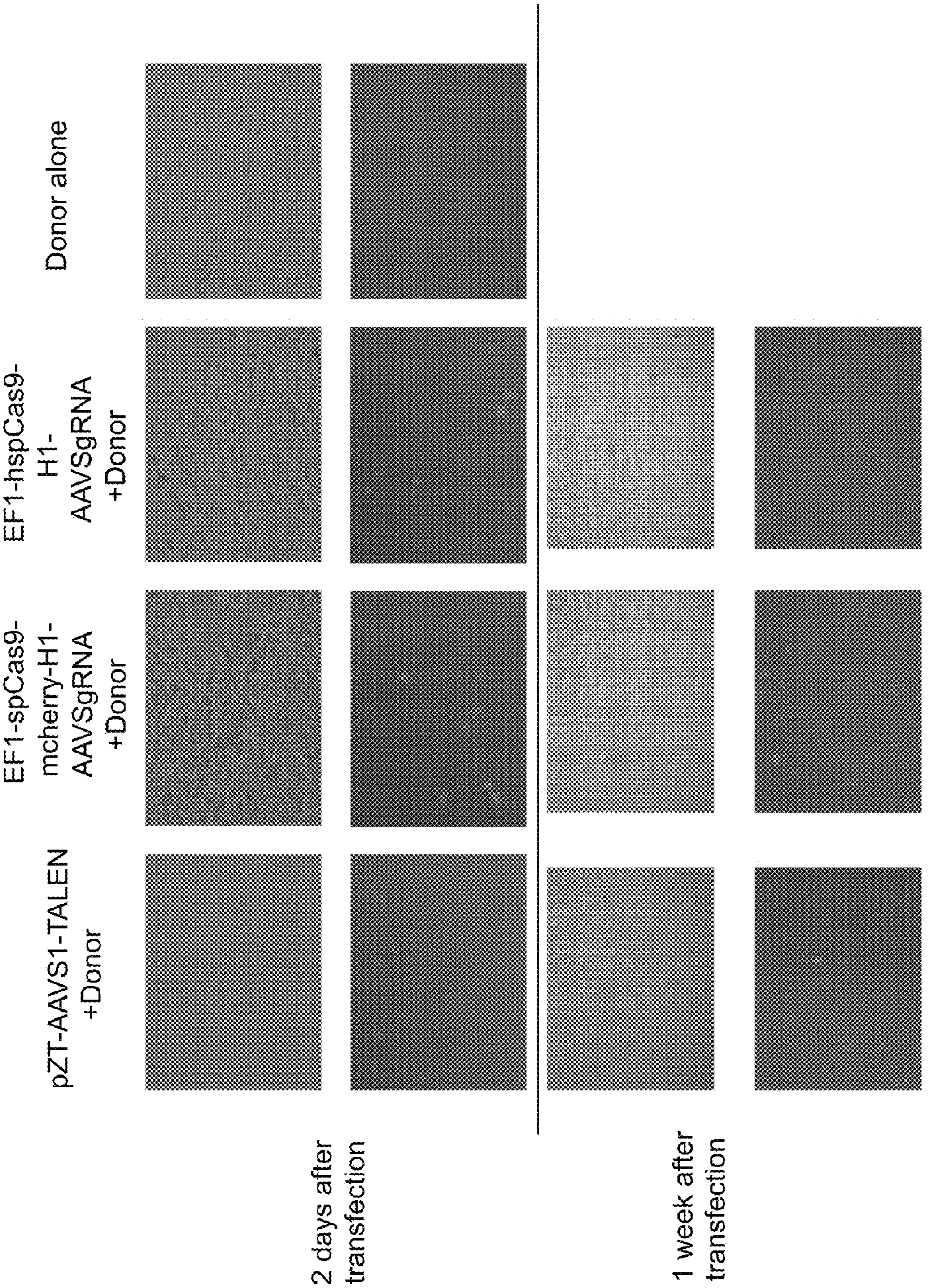
FIG. 4 provides fluorescent images of EGIP-293T cells following transfection of alternatively three expression constructs along with donor, and cells transfected with donor alone.

FIG. 4 provides fluorescent images following transfection of the various plasmids. It was observed that following the transfection of pZT-AAVS1-TALEN, EF1-hspCas9-H1-AAVSgRNA, and EF1-spCas9-mcherry-H1-AAVSgRNA constructs alone, the cells are EGFP negative. However, in the presence of donor, certain populations of the cells turn green. Both EF1-hspCas9-H1-AAVSgRNA and EF1-spCas9-mcherry-H1-AAVSgRNA in the presence of donor fragment show comparable or slightly higher HR rate as compared with pZT-AAVS1-TALEN.

Example 5

Figure 5:
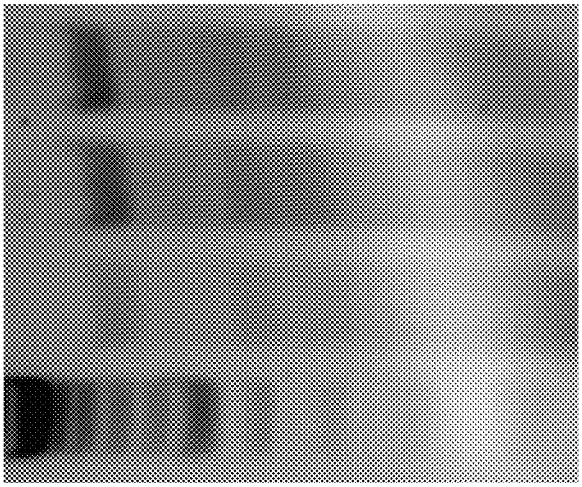
FIG. 5 provides a photograph of the results of a SURVEYOR® Mutation Detection Kit assay, measuring cleavage activity.

Comparison of Homologous Recombination Efficiencies of CRISPRII and TALEN Genomic Targeting Systems Using SURVEYOR® Cleavage Activity The SURVEYOR® Mutation Detection Kit assay (Transgenomic®, Inc.) also demonstrated that EF1-hspCas9-H1-AAVSgRNA and EF1-spCas9-mcherry-H1-AAVSgRNA alone can efficiently target AAVS fragment, and shows similar cleavage activity in comparison to pZT-AAVS1-TALEN. These results are shown in FIG. 5. Cleavage activity of human codon optimized all-in-one CRISPR II AAVS1 system (EF1-hspCas9-H1-AAVS) and prokaryote encoded all-in-one CRISPR II AAVS1 system (EF1-spCas9-mcherry-H1-AAVS) is compared to the activity of the pZT-AAVS1-TALEN system. From these data, it is estimated that the homologous recombination rate in EGIP 293T cells would be more than 8%, and the cleavage activity would be more than 25%. Therefore, both the human codon optimized all-in-one CRISPR II system and the prokaryote encoded all-in-one CRISPR II system are able to achieve genomic targeting and modification in a simple and highly efficient way.

Example 6

Demonstration of Homologous Recombination Activity of a Humanized CRISPRII Genomic Targeting System Using a Luciferase Reporter To further validate the all-in-one CRISPR II system, we designed a recombination monitoring system using the luciferase gene fragments as a target for genomic engineering, where the activity of the CRISPR II components can be monitored by either tracking luciferase activity or by SURVEYOR® Mutation Detection assay (Transgenomic®, Inc.). This assay system cloned and tested two different gRNAs which target the luciferase sequence.

For this purpose, a genomically engineered cell line stably expressing luciferase was established by infecting 293 cells with pGreenFire™ virus (System Biosciences, Inc.; Catalog No. TR010VA-1) and sorted for GFP positive cells (as both GFP and luciferase are coexpressed under the control of CMV promoter). These cells were then transfected with constructs expressing hspCas9 and luciferase gRNA, the constructs having the configuration shown in FIG. 6A. Two gRNAs which target the luciferase sequence were designed (FIG. 6B; Luc gRNA1 and Luc gRNA2; SEQ ID NOs: 13 and 14, respectively) and then cloned into the CRISPR all-in-one system expressing hspCas9 (FIG. 6A; termed EF1-hspCas9-H1-Luc).

The assay system also incorporated a donor fragment (FIG. 6C) which contains homology sequence flanking the luciferase gene, and therefore can replace the luciferase gene sequence with a red fluorescent protein (RFP) sequence. When the luciferase sequence is targeted by Cas9, in the presence of donor containing flanking dsGFP, RFP and flanking WPRE sequence, cells will turn RFP positive by homologous recombination (HR). The cleavage activity of the CRISPR II system can be monitored by using either the SURVEYOR® Mutation Detection assay (Transgenomic®, Inc.) or a luciferase assay. The homologous recombination activity can also be monitored by measuring RFP signal, as the genomic luciferase fragment would be replaced by RFP sequence (FIG. 6C).

The luciferase stable 293 cell line was transfected with either EF1-hspCas9-H1-Luc gRNA1 or EF1-hspCas9-H1-Luc gRNA2, and with or without donor. Three days after transfection, cells transfected with either EF1-hspCas9-H1-Luc gRNA1 alone or EF1-hspCas9-H1-Luc gRNA2 alone were collected for luciferase assay and SURVEYOR® assay.

Figure 7A:
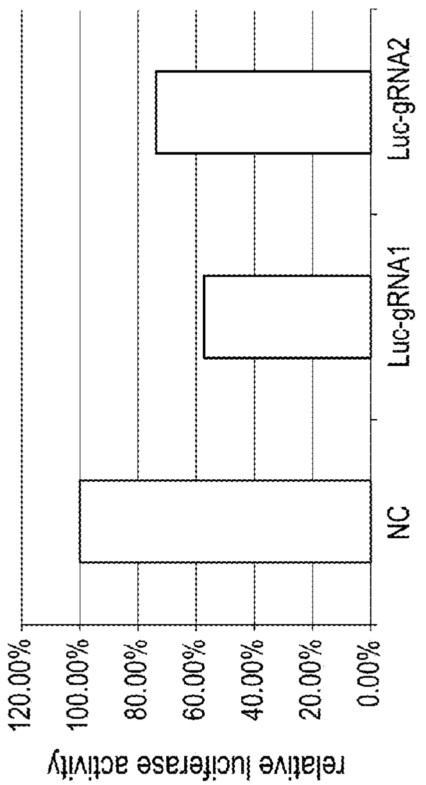
FIG. 7A provides a histogram depicting the results of a luciferase assay.

Cleavage activity of the human codon optimized all-in-one CRISPR II luciferase reporter system was assayed. It was observed that EF1-hspCas9-H1-Luc gRNA1 suppresses luciferase activity by 40% compared to untransfected negative control cells (NC). It was also observed that EF1-hspCas9-H1-Luc gRNA2 reduces luciferase activity by 25% compared to untransfected negative control cells (NC). See FIG. 7A.

Figure 7B:
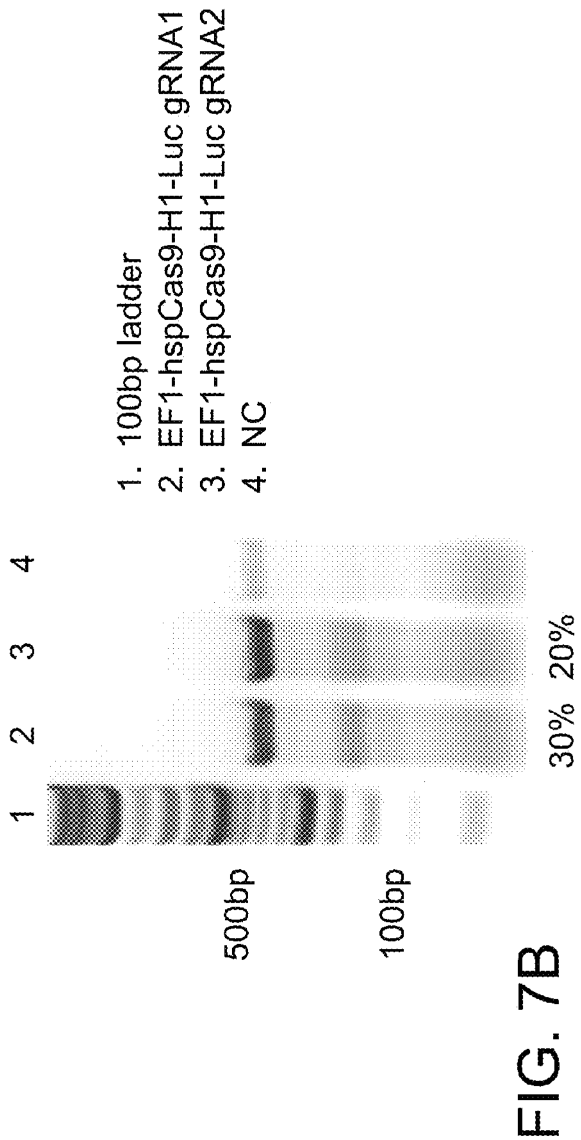
FIG. 7B provides a photograph of the results of a SURVEYOR® Mutation Detection Kit assay.

The SURVEYOR® assay showed results similar to the luciferase assay results. Cells transfected with EF1-hspCas9-H1-Luc gRNA1 showed 30% of the cleavage activity compared to untransfected cells, and cells transfected with the EF1-hspCas9-H1-Luc gRNA2 construct showed 22% of the cleavage activity contained in untransfected cells. See FIG. 7B.

Figure 8:
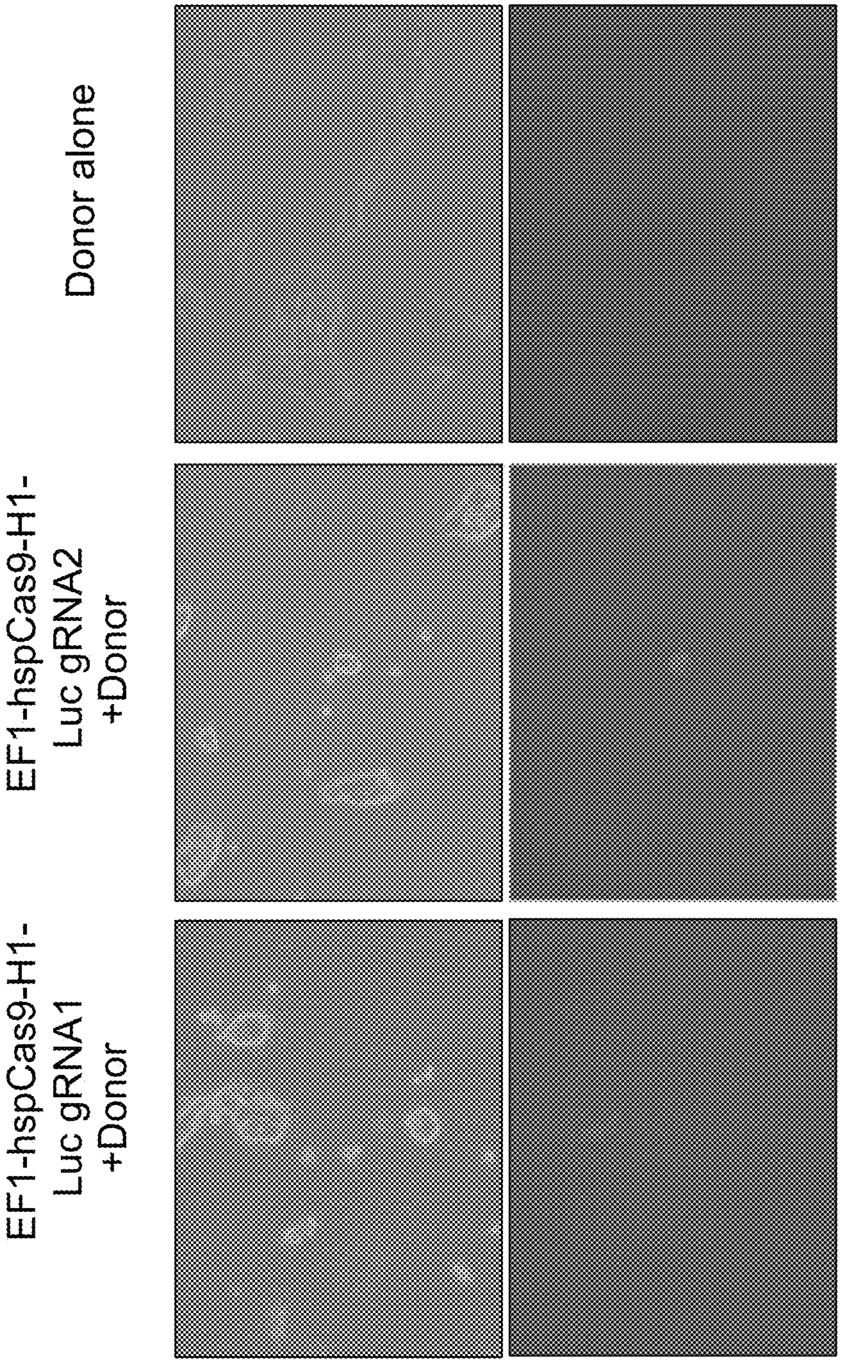
FIG. 8 provides fluorescent microscope images of cells transfected with either (i) EF1-hspCas9-H1-Luc gRNA1 and donor, (ii) cells transfected with EF1-hspCas9-H1-Luc gRNA2 and donor, or (iii) donor alone.

The efficiency of the homologous recombination event in the human codon optimized all-in-one CRISPR II luciferase system was also monitored by checking the RFP signal under a fluorescent microscope. Not surprising, RFP signal was detected in cells transfected with EF1-hspCas9-H1-Luc gRNA1 and donor, and also detected in cells transfected with EF1-hspCas9-H1-Luc gRNA2 and donor (FIG. 8).

This data further supports the notion that the engineered all-in-one CRISPR II system is a simple and robust system to achieve genomic editing.

Example 7

In Vitro Transcription Products of a Humanized CRISPRII Genomic Targeting System As described in the EXAMPLES above, the all-in-one CRISPR II system can be implemented in plasmid format. In addition, the components of the CRISPR II system can also be delivered in an mRNA format.

Figure 9:
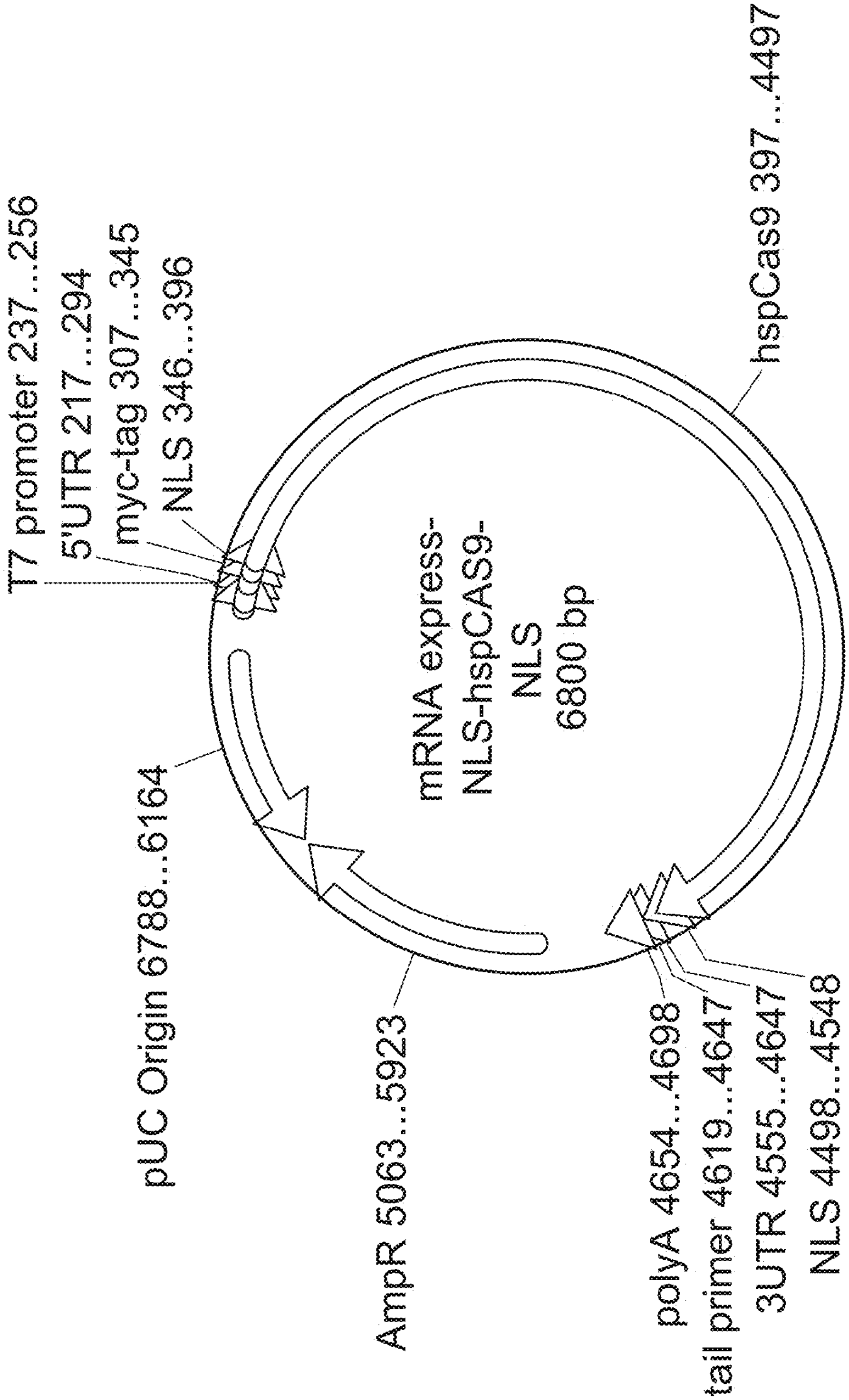
FIG. 9 provides a map of an mRNA expression vector for the expression of hspCas9 mRNA from a T7 promoter.

In order to generate in vitro transcribed CRISPR II system mRNA that can be delivered directly to cells without the need for plasmid delivery, the human codon optimized Cas9 polynucleotide was cloned into an mRNA expression vector construct, as shown in FIG. 9. This vector will express Cas9 from the T7 promoter, and will produce a Cas9 mRNA comprising two NLS sequences and a myc-tag. This will enable delivery of hspCas9 in mRNA format to achieve clean and highly efficient genomic modification.

The mRNA thus generated was tested in transfection experiments, and it was observed that the mRNA delivery is more efficient than plasmid DNA, especially in primary cells, stem cells and iPSCs. In view of this, it is contemplated that engineered hspCas9 mRNA will have broad applications such as ex vivo and in vivo gene therapy, regenerative medicine, and other applications.

Example 8 hspCas9 Sequence and Sequence Alignments

The nucleotide sequence of hspCas9 is provided in FIGS. 10A-10C and SEQ ID NO: 1. As shown in FIGS. 10A-10C, the initial ATG is indicated by double underline, and the terminal TGA stop codon is shown by dashed underline. The nucleotides comprising the myc-tag sequence are nucleotide positions 1 through 39, and are shown in lowercase letters. The nucleotides comprising the N-terminal and C-terminal nuclear localization signals (NLS) are nucleotide positions 40 through 90, and positions 4192 through 4242 (including the stop codon TGA), respectively, and are indicated by single underline.

FIG. 11 provides a nucleotide sequence alignment of two sequences, where the query sequence is the hspCas9 domain containing only the Cas9 coding region, without sequences encoding the myc-tag or NLS, i.e., the query sequence is nucleotide positions 91 through 4191 of the nucleotide sequence provided in FIGS. 10A-10C, and SEQ ID NO: 2. The subject sequence is a cas9sequence of Mali et al., "RNA-Guided Human Genome Engineering via Cas9," *Science Express* (Jan. 3, 2013); SEQ ID NO: 3.

FIG. 12 provides a nucleotide sequence alignment of two sequences, where the query sequence is the hspCas9 domain containing the N-terminal and C-terminal NLS, and without sequences encoding the myc-tag, i.e., the query sequence is nucleotide positions 40 through 4242 of the nucleotide sequence provided in FIGS. 10A-10C, and SEQ ID NO: 4. The subject sequence is a cas9 sequence of Cong et al., "Multiplex Genome Engineering Using CRISPR/Cas Systems," *Science Express* (Jan. 3, 2013); SEQ ID NO: 5.

* * *

While the foregoing disclosure has been described in some detail for purposes of clarity and understanding, it will be clear to one skilled in the art from a reading of this disclosure that various changes in form and detail can be made without departing from the true scope of the invention. It is to be understood that the invention is not limited to any of the specifically recited methodologies, reagents or instrumentation that are recited herein, where similar methodologies, reagents or instrumentation can be substituted and used in the construction and practice of the invention, and remain within the scope of the invention. It is also to be understood that the description and terminology used in the present disclosure is for the purpose of describing particular embodiments of the invention only, and is not intended that the invention be limited solely to the embodiments described herein.

As used in this specification and the appended claims, singular forms such as "a", "an" and "the" include plural referents unless the content clearly dictates otherwise. For example, reference to "a plasmid" includes a plurality of plasmids; reference to "a cell" also refers to cultures or populations of cells. All industry and technical terms used herein have the same meaning as commonly understood by one of ordinary skill in the art or industry to which the invention pertains, unless defined otherwise.

What is claimed is:

1. An expression construct comprising:

(a) a first polynucleotide encoding a Cas9 protein, wherein the first polynucleotide comprises the nucleotide sequence of positions 91 through 4191 of SEQ ID NO: 1, and (b) a second polynucleotide encoding a guide RNA, said guide RNA comprising (i) a crRNA-tracrRNA chimeric transcript comprising the nucleotide sequence of positions 49 through 131 of SEQ ID NO: 6, and (ii) a targeting sequence complementary to a target nucleic acid, where the targeting sequence is operably linked to the crRNA-tracrRNA chimeric transcript.

2. The expression construct of claim 1, wherein the expression construct is a mammalian expression construct.

3. The expression construct of claim 1, wherein the Cas9 protein is a *Streptococcus pyogenes* Cas9 protein.

4. The expression construct of claim 1, wherein the first polynucleotide further encodes at least one nuclear localization signal.

5. The expression construct of claim 1, wherein the first polynucleotide comprises the nucleotide sequence of positions 40 through 4242 of SEQ ID NO: 1.

6. A system for cleavage of a target nucleic acid in a mammalian cell, the system comprising:

(a) a mammalian expression construct comprising:

i) a first polynucleotide encoding a Cas9 protein, wherein the first polynucleotide comprises the nucleotide sequence of positions 91 through 4191 of SEQ ID NO: 1, and ii) a second polynucleotide encoding a guide RNA, said guide RNA comprising:

(A) a crRNA-tracrRNA chimeric transcript comprising the nucleotide sequence of positions 49 through 131 of SEQ ID NO: 6, and (B) a targeting sequence complementary to the target nucleic acid, where the targeting sequence is operably linked to the crRNA-tracrRNA chimeric transcript; and, (b) a mammalian cell comprising the target nucleic acid, wherein the first polynucleotide and second polynucleotide are capable of expression from the mammalian expression construct when that construct is within the mammalian cell.

7. The system of claim 6, wherein the cleavage is a double stranded break.

8. The system of claim 6, wherein the target nucleic acid is a genomic nucleic acid.

9. The system of claim 6, wherein the target nucleic acid is complementary to an endogenous mammalian nucleotide sequence.

10. The system of claim 6, wherein the system is a multiplex system, further comprising at least a second guide RNA for cleavage of a second target nucleic acid in the mammalian cell, the second guide RNA comprising:

(A) a second crRNA-tracrRNA chimeric transcript, and (B) a second targeting sequence complementary to the second target nucleic acid, where the second targeting sequence is operably linked to the crRNA-tracrRNA chimeric transcript.

11. A system for modification of a genomic target nucleic acid in a mammalian cell, the system comprising:

(a) a mammalian expression construct comprising:

i) a first polynucleotide encoding a Cas9 protein, wherein the first polynucleotide comprises the nucleotide sequence of positions 91 through 4191 of SEQ ID NO: 1, and ii) a second polynucleotide encoding a guide RNA, said guide RNA comprising:

(A) a crRNA-tracrRNA chimeric transcript comprising the nucleotide sequence of positions 49 through 131 of SEQ ID NO: 6, and (B) a targeting sequence complementary to the genomic target nucleic acid, where the targeting sequence is operably linked to the crRNA-tracrRNA chimeric transcript;

(b) a donor polynucleotide comprising nucleotide sequence having homology to the genomic target nucleic acid or homology to nucleotide sequence flanking the genomic target nucleic acid; and (c) a mammalian cell comprising the genomic target nucleic acid, wherein the first polynucleotide and second polynucleotide are capable of expression from the mammalian expression construct when that construct is within the mammalian cell.

12. The system of claim 11, wherein the genomic target nucleic acid is an endogenous mammalian nucleotide sequence.

13. The system of claim 11, wherein the system is a multiplex system, further comprising at least a second guide RNA comprising a crRNA-tracrRNA chimeric transcript operably linked to a second targeting sequence complementary to a second genomic target nucleic acid.

14. The system of claim 11, wherein the mammalian expression construct further comprises at least one nucleotide sequence that permits the identification or selection of mammalian cells that contain a modification of the genomic target nucleic acid.

15. The system of claim 11, wherein the modification of the genomic target nucleic acid is a replacement of nucleotides from the genomic target with nucleotides encoded by the donor polynucleotide.

* * * * *

SEQUENCE LISTING

```
<160> NUMBER OF SEQ ID NOS: 14

<210> SEQ ID NO 1
<211> LENGTH: 4242
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atggctagta tgcagaaact gattagtgaa gaggacctga tggctcccaa gaagaagcga     60

aaggtgggca tccacggcgt gcccgctgcc gacaaaaagt atagtatcgg actggatatt    120
```

-continued ggcactaaca gcgtgggatg ggccgtcatc accgacgagt acaaagtgcc aagcaagaag 180
ttcaaggtcc tgggaaacac cgatagacac agtatcaaga aaaatctgat tggagccctg 240
ctgttcgact caggggagac agctgaagca actaggctga aaagaacagc taggagacgg 300
tatactcgcc gaaagaatcg gatctgctac ctccaggaga ttttctccaa cgaaatggcc 360
aaggtggacg atagtttctt tcatcgcctg gaggaatcat tcctggtcga ggaagataag 420
aaacacgaga ggcatcccat ctttggcaac attgtggacg aggtcgctta tcacgaaaag 480
taccctacaa tctatcatct gcggaagaaa ctggtggaca gcactgataa ggcagacctg 540
cgcctgatct atctggccct ggctcacatg attaagttca gggggcattt tctgatcgag 600
ggcgatctga acccagacaa ttccgatgtg gacaagctgt tcatccagct ggtccagaca 660
tacaatcagc tgtttgagga aaaccccatt aatgcatctg gggtggacgc aaaagccatc 720
ctgagtgcca gactgtctaa gagtaggaga ctggagaacc tgatcgctca gctgccaggc 780
gaaaagaaaa acggcctgtt tggaaatctg attgcactgt cactgggact gacccccaac 840
ttcaagagca attttgatct ggccgaggac gctaagctcc agctgagcaa ggacacctac 900
gacgatgacc tggataacct gctggctcag atcggcgatc agtacgcaga cctgttcctg 960
gccgctaaga atctgtctga cgccatcctg ctgagtgata ttctgagagt gaacaccgag 1020
attacaaaag cccccctgtc agctagcatg atcaagagat atgacgagca ccatcaggat 1080
ctgaccctgc tgaaggctct ggtgcggcag cagctgcctg agaagtacaa agaaatcttc 1140
tttgatcaga gcaagaatgg gtacgccggc tatattgacg gcggagcttc ccaggaggag 1200
ttctacaagt ttatcaaacc tattctggag aagatggacg gcactgagga actgctggtg 1260
aaactgaatc gggaagacct gctgcggaag cagcgcacct tcgataacgg cagcatccct 1320
caccagattc atctgggaga gctgcacgca atcctgcggc gccaggaaga cttctaccca 1380
tttctgaagg ataaccggga gaagatcgaa aaaattctga ctttccgcat cccctactat 1440
gtggggcctc tggcaagagg caattcccgg tttgcctgga tgacccgcaa gtctgaggaa 1500
acaatcactc cctggaactt cgaggaagtg gtcgataagg gcgcttccgc acagtctttc 1560
attgagagga tgacaaattt tgacaagaac ctgccaaatg aaaaagtgct gcccaagcac 1620
agcctgctgt acgagtattt caccgtctat aacgaactga caaaggtgaa atacgtcact 1680
gagggcatga gaaagcctgc cttcctgtcc ggagaacaga agaaagctat cgtggacctg 1740
ctgtttaaaa ccaatcggaa ggtgacagtc aagcagctga aagaggacta cttcaagaaa 1800
attgaatgtt tcgattctgt ggagatcagt ggggtcgaag acaggtttaa cgcctctctg 1860
ggcacctacc acgatctgct gaagatcatt aaggataaag acttcctgga caacgaggaa 1920
aatgaggaca tcctggagga cattgtgctg accctgacac tgtttgagga tcgggaaatg 1980
atcgaggaac gcctgaagac ctacgcccat ctgttcgatg acaaagtgat gaaacagctg 2040
aagcgaagga gatacactgg gtggggccga ctgagcagga agctgatcaa tggcattcgc 2100
gacaaacaga gtggaaagac aatcctggac tttctgaagt cagatggctt cgctaacagg 2160
aattttatgc agctgattca cgatgactct ctgactttca aagaggacat ccagaaggca 2220
caggtgtccg gacaggggga ctctctgcac gagcatatcg caaacctggc cgggagccct 2280
gccatcaaga aaggcatcct ccagaccgtg aaggtggtgg acgagctggt gaaagtcatg 2340
ggaagacata agccagaaaa catcgtgatt gagatggcca gggagaatca gaccacacag 2400
aaagggcaga agaactctcg ggagcgcatg aaacgcatcg aggaaggaat taaggaactg 2460
gggagtcaga tcctgaaaga gcaccccgtg gaaaacacac agctccagaa tgagaagctg 2520

```
tatctgtact acctccagaa tggccgcgat atgtacgtgg accaggagct ggatattaac   2580
cgactgtcag attatgacgt ggatcatatc gtcccacagt cattcctgaa agatgacagc   2640
attgacaata aggtgctgac ccgcagcgac aaaaaccgag gaaagagtga taatgtcccc   2700
tcagaggaag tggtcaagaa aatgaagaac tactggaggc agctgctgaa tgccaaactg   2760
atcacccagc gaaagtttga taacctgaca aaagctgaga ggggggcct gtccgaactg   2820
gacaaagcag gcttcatcaa gcgacagctg gtggagacaa ggcagatcac aaagcacgtc   2880
gctcagatcc tggacagcag gatgaacacc aagtacgatg agaatgacaa actgatccgg   2940
gaagtgaagg tcattacact gaagtcaaaa ctggtgagcg actttaggaa agatttccag   3000
ttctacaagg tcagagagat caacaactac caccatgctc atgacgcata cctgaacgca   3060
gtggtcggga ctgccctgat taagaaatac cctaaactgg agtctgagtt cgtgtacggc   3120
gactataagg tgtacgatgt cagaaaaatg atcgccaaga gcgagcagga aattggcaaa   3180
gccaccgcta agtatttctt ttactccaac atcatgaatt tctttaagac tgagatcacc   3240
ctggcaaatg gcgaaatccg aaagaggcca ctgattgaga ctaacggaga gacaggggaa   3300
atcgtgtggg acaaaggaag agattttgct accgtgcgga aggtcctgag tatgccccaa   3360
gtgaatattg tcaagaaaac agaggtgcag actggagggt tcagtaagga atcaattctg   3420
cctaaacgca acagcgataa gctgatcgcc cgaaagaaag actgggaccc caagaagtat   3480
ggcggattcg actccccaac cgtggcttac tctgtcctgg tggtcgcaaa ggtggagaag   3540
ggaaaaagca agaaactgaa atccgtcaag gaactgctgg ggatcacaat tatggagagg   3600
agcagcttcg aaaagaatcc tatcgatttt ctggaggcca aagggtataa ggaagtgaag   3660
aaagacctga tcatcaagct gccaaagtac tctctgtttg agctggaaaa cggcagaaag   3720
cggatgctgg caagtgccgg cgagctgcaa aaaggaaatg aactggccct gccctcaaag   3780
tacgtgaact tcctgtatct ggctagccac tacgagaagc tgaaaggctc ccctgaggat   3840
aacgaacaga aacagctgtt tgtggagcag cacaagcatt atctggacga gatcattgaa   3900
cagattagcg agttctccaa acgcgtgatc ctggctgacg caaatctgga taaggtcctg   3960
tctgcataca acaaacacag ggacaagcca atcagagagc aggccgaaaa tatcattcat   4020
ctgttcactc tgaccaacct gggagccccc gcagccttca agtattttga cactaccatc   4080
gatcgcaaac gatacacaag cactaaggag gtgctggatg ctaccctgat ccaccagagc   4140
attactgggc tgtacgagac aaggatcgac ctgtcccagc tgggggaga caaacgccca   4200
gccgccacca agaaagcagg acaggcaaag aagaagaagt ga                      4242
```

```
<210> SEQ ID NO 2
<211> LENGTH: 4102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

gacaaaaagt atagtatcgg actggatatt ggcactaaca gcgtgggatg ggccgtcatc     60
accgacgagt acaaagtgcc aagcaagaag ttcaaggtcc tgggaaacac cgatagacac    120
agtatcaaga aaaatctgat tggagccctg ctgttcgact caggggagac agctgaagca    180
actaggctga aaagaacagc taggagacgg tatactcgcc gaaagaatcg gatctgctac    240
ctccaggaga ttttctccaa cgaaatggcc aaggtggacg atagtttctt tcatcgcctg    300
```

-continued

```
gaggaatcat tcctggtcga ggaagataag aaacacgaga ggcatcccat ctttggcaac    360
attgtggacg aggtcgctta tcacgaaaag taccctacaa tctatcatct gcggaagaaa    420
ctggtggaca gcactgataa ggcagacctg cgcctgatct atctggccct ggctcacatg    480
attaagttca gggggcattt tctgatcgag ggcgatctga acccagacaa ttccgatgtg    540
gacaagctgt tcatccagct ggtccagaca tacaatcagc tgtttgagga aaacccccatt    600
aatgcatctg ggtggacgc aaaagccatc ctgagtgcca gactgtctaa gagtaggaga    660
ctggagaacc tgatcgctca gctgccaggc gaaaagaaaa acggcctgtt tggaaatctg    720
attgcactgt cactgggact gacccccaac ttcaagagca attttgatct ggccgaggac    780
gctaagctcc agctgagcaa ggacacctac gacgatgacc tggataacct gctggctcag    840
atcggcgatc agtacgcaga cctgttcctg gccgctaaga atctgtctga cgccatcctg    900
ctgagtgata ttctgagagt gaacaccgag attacaaaag ccccccctgtc agctagcatg    960
atcaagagat atgacgagca ccatcaggat ctgaccctgc tgaaggctct ggtgcggcag   1020
cagctgcctg agaagtacaa agaaatcttc tttgatcaga gcaagaatgg gtacgccggc   1080
tatattgacg gcggagcttc ccaggaggag ttctacaagt ttatcaaacc tattctggag   1140
aagatggacg gcactgagga actgctggtg aaactgaatc gggaagacct gctgcggaag   1200
cagcgcacct tcgataacgg cagcatccct caccagattc atctgggaga gctgcacgca   1260
atcctgcggc gccaggaaga cttctaccca tttctgaagg ataaccggga gaagatcgaa   1320
aaaattctga ctttccgcat cccctactat gtggggcctc tggcaagagg caattcccgg   1380
tttgcctgga tgacccgcaa gtctgaggaa acaatcactc cctggaactt cgaggaagtg   1440
gtcgataagg gcgcttccgc acagtctttc attgagagga tgacaaattt tgacaagaac   1500
ctgccaaatg aaaaagtgct gcccaagcac agcctgctgt acgagtattt caccgtctat   1560
aacgaactga caaaggtgaa atacgtcact gagggcatga gaaagcctgc cttcctgtcc   1620
ggagaacaga agaaagctat cgtggacctg ctgtttaaaa ccaatcggaa ggtgacagtc   1680
aagcagctga aagaggacta cttcaagaaa attgaatgtt tcgattctgt ggagatcagt   1740
ggggtcgaag acaggtttaa cgcctctctg ggcacctacc acgatctgct gaagatcatt   1800
aaggataaag acttcctgga caacgaggaa aatgaggaca tcctggagga cattgtgctg   1860
accctgacac tgtttgagga tcgggaaatg atcgaggaac gcctgaagac ctacgcccat   1920
ctgttcgatg acaaagtgat gaaacagctg aagcgaagga gatacactgg gtggggccga   1980
ctgagcagga agctgatcaa tggcattcgc gacaaacaga gtggaaagac aatcctggac   2040
tttctgaagt cagatggctt cgctaacagg aattttatgc agctgattca cgatgactct   2100
ctgactttca aagaggacat ccagaaggca caggtgtccg gacaggggga ctctctgcac   2160
gagcatatcg caaacctggc cgggagccct gccatcaaga aaggcatcct ccagaccgtg   2220
aaggtggtgg acgagctggt gaaagtcatg ggaagacata agccagaaaa catcgtgatt   2280
gagatggcca gggagaatca gaccacacag aaagggcaga agaactctcg ggagcgcatg   2340
aaacgcatcg aggaaggaat taaggaactg gggagtcaga tcctgaaaga gcaccccgtg   2400
gaaaacacac agctccagaa tgagaagctg tatctgtact acctccagaa tggccgcgat   2460
atgtacgtgg accaggagct ggatattaac cgactgtcag attatgacgt ggatcatatc   2520
gtcccacagt cattcctgaa agatgacagc attgacaata aggtgctgac ccgcagcgac   2580
aaaaaccgag gaaagagtga taatgtcccc tcagaggaag tggtcaagaa aatgaagaac   2640
```

-continued

```
tactggaggc agctgctgaa tgccaaactg atcacccagc gaaagtttga taacctgaca   2700

aaagctgaga ggggggcct gtccgaactg gacaaagcag gcttcatcaa gcgacagctg   2760

gtggagacaa ggcagatcac aaagcacgtc gctcagatcc tggacagcag gatgaacacc   2820

aagtacgatg agaatgacaa actgatccgg gaagtgaagg tcattacact gaagtcaaaa   2880

ctggtgagcg actttaggaa agatttccag ttctacaagg tcagagagat caacaactac   2940

caccatgctc atgacgcata cctgaacgca gtggtcggga ctgccctgat taagaaatac   3000

cctaaactgg agtctgagtt cgtgtacggc gactataagg tgtacgatgt cagaaaaatg   3060

atcgccaaga gcgagcagga aattggcaaa gccaccgcta agtatttctt ttactccaac   3120

atcatgaatt tctttaagac tgagatcacc ctggcaaatg gcgaaatccg aaagaggcca   3180

ctgattgaga ctaacggaga gacaggggaa atcgtgtggg acaaaggaag agattttgct   3240

accgtgcgga aggtcctgag tatgccccaa gtgaatattg tcaagaaaac agaggtgcag   3300

actggagggt tcagtaagga atcaattctg cctaaacgca acagcgataa gctgatcgcc   3360

cgaaagaaag actgggaccc caagaagtat ggcggattcg actccccaac cgtggcttac   3420

tctgtcctgg tggtcgcaaa ggtggagaag ggaaaaagca agaaactgaa atccgtcaag   3480

gaactgctgg ggatcacaat tatggagagg agcagcttcg aaaagaatcc tatcgatttt   3540

ctggaggcca aagggtataa ggaagtgaag aaagacctga tcatcaagct gccaaagtac   3600

tctctgtttg agctggaaaa cggcagaaag cggatgctgg caagtgccgg cgagctgcaa   3660

aaaggaaatg aactggccct gccctcaaag tacgtgaact tcctgtatct ggctagccac   3720

tacgagaagc tgaaaggctc ccctgaggat aacgaacaga aacagctgtt tgtggagcag   3780

cacaagcatt atctggacga gatcattgaa cagattagcg agttctccaa acgcgtgatc   3840

ctggctgacg caaatctgga taaggtcctg tctgcataca acaaacacag ggacaagcca   3900

atcagagagc aggccgaaaa tatcattcat ctgttcactc tgaccaacct gggagccccc   3960

gcagccttca agtattttga cactaccatc gatcgcaaac gatacacaag cactaaggag   4020

gtgctggatg ctaccctgat ccaccagagc attactgggc tgtacgagac aaggatcgac   4080

ctgtcccagc tgggggaga ca                                              4102


<210> SEQ ID NO 3
<211> LENGTH: 4102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

gacaagaagt actccattgg gctcgatatc ggcacaaaca gcgtcggctg ggccgtcatt     60

acggacgagt acaaggtgcc gagcaaaaaa ttcaaagttc tgggcaatac cgatcgccac    120

agcataaaga agaacctcat tggcgccctc ctgttcgact ccggggagac ggccgaagcc    180

acgcggctca aaagaacagc acggcgcaga tatacccgca gaaagaatcg gatctgctac    240

ctgcaggaga tctttagtaa tgagatggct aaggtggatg actctttctt ccataggctg    300

gaggagtcct ttttggtgga ggaggataaa aagcacgagc gccacccaat ctttggcaat    360

atcgtggacg aggtggcgta ccatgaaaag tacccaacca tatatcatct gaggaagaag    420

cttgtagaca gtactgataa ggctgacttg cggttgatct atctcgcgct ggcgcatatg    480

atcaaatttc ggggacactt cctcatcgag ggggacctga acccagacaa cagcgatgtc    540
```

-continued

```
gacaaactct ttatccaact ggttcagact tacaatcagc ttttcgaaga gaacccgatc    600
aacgcatccg gagttgacgc caaagcaatc ctgagcgcta ggctgtccaa atcccggcgg    660
ctcgaaaacc tcatcgcaca gctccctggg gagaagaaga acggcctgtt tggtaatctt    720
atcgccctgt cactcgggct gacccccaac tttaaatcta acttcgacct ggccgaagat    780
gccaagcttc aactgagcaa agacacctac gatgatgatc tcgacaatct gctggcccag    840
atcggcgacc agtacgcaga cctttttttg gcggcaaaga acctgtcaga cgccattctg    900
ctgagtgata ttctgcgagt gaacacggag atcaccaaag ctccgctgag cgctagtatg    960
atcaagcgct atgatgagca ccaccaagac ttgactttgc tgaaggccct tgtcagacag   1020
caactgcctg agaagtacaa ggaaattttc ttcgatcagt ctaaaaatgg ctacgccgga   1080
tacattgacg gcggagcaag ccaggaggaa ttttacaaat ttattaagcc catcttggaa   1140
aaaatggacg gcaccgagga gctgctggta aagcttaaca gagaagatct gttgcgcaaa   1200
cagcgcactt tcgacaatgg aagcatcccc caccagattc acctgggcga actgcacgct   1260
atcctcaggc ggcaagagga tttctacccc tttttgaaag ataacaggga aaagattgag   1320
aaaatcctca catttcggat accctactat gtaggccccc tcgcccgggg aaattccaga   1380
ttcgcgtgga tgactcgcaa atcagaagag accatcactc cctggaactt cgaggaagtc   1440
gtggataagg gggcctctgc ccagtccttc atcgaaagga tgactaactt tgataaaaat   1500
ctgcctaacg aaaaggtgct tcctaaacac tctctgctgt acgagtactt cacagtttat   1560
aacgagctca ccaaggtcaa atacgtcaca gaagggatga gaaagccagc attcctgtct   1620
ggagagcaga agaaagctat cgtggacctc ctcttcaaga cgaaccggaa agttaccgtg   1680
aaacagctca aagaagacta tttcaaaaag attgaatgtt tcgactctgt tgaaatcagc   1740
ggagtggagg atcgcttcaa cgcatccctg ggaacgtatc acgatctcct gaaaatcatt   1800
aaagacaagg acttcctgga caatgaggag aacgaggaca ttcttgagga cattgtcctc   1860
acccttacgt tgtttgaaga tagggagatg attgaagaac gcttgaaaac ttacgctcat   1920
ctcttcgacg acaaagtcat gaaacagctc aagaggcgcc gatatacagg atgggggcgg   1980
ctgtcaagaa aactgatcaa tgggatccga gacaagcaga gtggaaagac aatcctggat   2040
tttcttaagt ccgatggatt tgccaaccgg aacttcatgc agttgatcca tgatgactct   2100
ctcaccttta aggaggacat ccagaaagca caagtttctg gccaggggga cagtcttcac   2160
gagcacatcg ctaatcttgc aggtagccca gctatcaaaa agggaatact gcagaccgtt   2220
aaggtcgtgg atgaactcgt caaagtaatg ggaaggcata agcccgagaa tatcgttatc   2280
gagatggccc gagagaacca aactacccag aagggacaga agaacagtag ggaaaggatg   2340
aagaggattg aagagggtat aaaagaactg gggtcccaaa tccttaagga acacccagtt   2400
gaaaacaccc agcttcagaa tgagaagctc tacctgtact acctgcagaa cggcagggac   2460
atgtacgtgg atcaggaact ggacatcaat cggctctccg actacgacgt ggatcatatc   2520
gtgccccagt cttttctcaa agatgattct attgataata aagtgttgac aagatccgat   2580
aaaaatagag ggaagagtga taacgtcccc tcagaagaag ttgtcaagaa aatgaaaaat   2640
tattggcggc agctgctgaa cgccaaactg atcacacaac ggaagttcga taatctgact   2700
aaggctgaac gaggtggcct gtctgagttg gataaagccg gcttcatcaa aaggcagctt   2760
gttgagacac gccagatcac caagcacgtg gcccaaattc tcgattcacg catgaacacc   2820
aagtacgatg aaaatgacaa actgattcga gaggtgaaag ttattactct gaagtctaag   2880
ctggtctcag atttcagaaa ggactttcag ttttataagg tgagagagat caacaattac   2940
```

caccatgcgc atgatgccta cctgaatgca gtggtaggca ctgcacttat caaaaaatat 3000
cccaagcttg aatctgaatt tgtttacgga gactataaag tgtacgatgt taggaaaatg 3060
atcgcaaagt ctgagcagga aataggcaag gccaccgcta agtacttctt ttacagcaat 3120
attatgaatt ttttcaagac cgagattaca ctggccaatg gagagattcg gaagcgacca 3180
cttatcgaaa caaacggaga aacaggagaa atcgtgtggg acaagggtag ggatttcgcg 3240
acagtccgga aggtcctgtc catgccgcag gtgaacatcg ttaaaaagac cgaagtacag 3300
accggaggct tctccaagga aagtatcctc ccgaaaagga acagcgacaa gctgatcgca 3360
cgcaaaaaag attgggaccc caagaaatac ggcggattcg attctcctac agtcgcttac 3420
agtgtactgg ttgtggccaa agtggagaaa gggaagtcta aaaaactcaa aagcgtcaag 3480
gaactgctgg gcatcacaat catggagcga tcaagcttcg aaaaaaaccc catcgacttt 3540
ctcgaggcga aaggatataa agaggtcaaa aaagacctca tcattaagct tcccaagtac 3600
tctctctttg agcttgaaaa cggccggaaa cgaatgctcg ctagtgcggg cgagctgcag 3660
aaaggtaacg agctggcact gccctctaaa tacgttaatt tcttgtatct ggccagccac 3720
tatgaaaagc tcaaagggtc tcccgaagat aatgagcaga agcagctgtt cgtggaacaa 3780
cacaaacact accttgatga gatcatcgag caaataagcg aattctccaa aagagtgatc 3840
ctcgccgacg ctaacctcga taaggtgctt tctgcttaca ataagcacag ggataagccc 3900
atcagggagc aggcagaaaa cattatccac ttgtttactc tgaccaactt gggcgcgcct 3960
gcagccttca agtacttcga caccaccata gacagaaagc ggtacacctc tacaaaggag 4020
gtcctggacg ccacactgat tcatcagtca attacggggc tctatgaaac aagaatcgac 4080
ctctctcagc tcggtggaga ca 4102

<210> SEQ ID NO 4
<211> LENGTH: 4203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
atggctccca agaagaagcg aaaggtgggc atccacggcg tgcccgctgc cgacaaaaag 60
tatagtatcg gactggatat tggcactaac agcgtgggat gggccgtcat caccgacgag 120
tacaaagtgc caagcaagaa gttcaaggtc ctgggaaaca ccgatagaca cagtatcaag 180
aaaaatctga ttggagccct gctgttcgac tcaggggaga cagctgaagc aactaggctg 240
aaaagaacag ctaggagacg gtatactcgc cgaaagaatc ggatctgcta cctccaggag 300
attttctcca acgaaatggc caaggtggac gatagtttct ttcatcgcct ggaggaatca 360
ttcctggtcg aggaagataa gaaacacgag aggcatccca tctttggcaa cattgtggac 420
gaggtcgctt atcacgaaaa gtaccctaca atctatcatc tgcggaagaa actggtggac 480
agcactgata aggcagacct gcgcctgatc tatctggccc tggctcacat gattaagttc 540
agggggcatt ttctgatcga gggcgatctg aacccagaca attccgatgt ggacaagctg 600
ttcatccagc tggtccagac atacaatcag ctgtttgagg aaaaccccat taatgcatct 660
ggggtggacg caaaagccat cctgagtgcc agactgtcta agagtaggag actggagaac 720
ctgatcgctc agctgccagg cgaaaagaaa aacggcctgt ttggaaatct gattgcactg 780
tcactgggac tgacccccaa cttcaagagc aattttgatc tggccgagga cgctaagctc 840
cagctgagca aggacaccta cgacgatgac ctggataacc tgctggctca gatcggcgat 900
cagtacgcag acctgttcct ggccgctaag aatctgtctg acgccatcct gctgagtgat 960
attctgagag tgaacaccga gattacaaaa gcccccctgt cagctagcat gatcaagaga 1020
tatgacgagc accatcagga tctgaccctg ctgaaggctc tggtgcggca gcagctgcct 1080
gagaagtaca aagaaatctt ctttgatcag agcaagaatg ggtacgccgg ctatattgac 1140
ggcggagctt cccaggagga gttctacaag tttatcaaac ctattctgga gaagatggac 1200
ggcactgagg aactgctggt gaaactgaat cgggaagacc tgctgcggaa gcagcgcacc 1260
ttcgataacg gcagcatccc tcaccagatt catctgggag agctgcacgc aatcctgcgg 1320
cgccaggaag acttctaccc atttctgaag gataaccggg agaagatcga aaaaattctg 1380
actttccgca tcccctacta tgtggggcct ctggcaagag gcaattcccg gtttgcctgg 1440
atgacccgca agtctgagga aacaatcact ccctggaact tcgaggaagt ggtcgataag 1500
ggcgcttccg cacagtcttt cattgagagg atgacaaatt ttgacaagaa cctgccaaat 1560
gaaaaagtgc tgcccaagca cagcctgctg tacgagtatt tcaccgtcta taacgaactg 1620
acaaaggtga aatacgtcac tgagggcatg agaaagcctg ccttcctgtc cggagaacag 1680
aagaaagcta tcgtggacct gctgtttaaa accaatcgga aggtgacagt caagcagctg 1740
aaagaggact acttcaagaa aattgaatgt ttcgattctg tggagatcag tggggtcgaa 1800
gacaggttta acgcctctct gggcacctac cacgatctgc tgaagatcat taaggataaa 1860
gacttcctgg acaacgagga aaatgaggac atcctggagg acattgtgct gaccctgaca 1920
ctgtttgagg atcgggaaat gatcgaggaa cgcctgaaga cctacgccca tctgttcgat 1980
gacaaagtga tgaaacagct gaagcgaagg agatacactg ggtggggccg actgagcagg 2040
aagctgatca atggcattcg cgacaaacag agtggaaaga caatcctgga ctttctgaag 2100
tcagatggct tcgctaacag gaattttatg cagctgattc acgatgactc tctgactttc 2160
aaagaggaca tccagaaggc acaggtgtcc ggacaggggg actctctgca cgagcatatc 2220
gcaaacctgg ccgggagccc tgccatcaag aaaggcatcc tccagaccgt gaaggtggtg 2280
gacgagctgg tgaaagtcat gggaagacat aagccagaaa acatcgtgat tgagatggcc 2340
agggagaatc agaccacaca gaaagggcag aagaactctc gggagcgcat gaaacgcatc 2400
gaggaaggaa ttaaggaact ggggagtcag atcctgaaag agcaccccgt ggaaaacaca 2460
cagctccaga atgagaagct gtatctgtac tacctccaga atggccgcga tatgtacgtg 2520
gaccaggagc tggatattaa ccgactgtca gattatgacg tggatcatat cgtcccacag 2580
tcattcctga aagatgacag cattgacaat aaggtgctga cccgcagcga caaaaaccga 2640
ggaaagagtg ataatgtccc ctcagaggaa gtggtcaaga aaatgaagaa ctactggagg 2700
cagctgctga atgccaaact gatcacccag cgaaagtttg ataacctgac aaaagctgag 2760
aggggggggc tgtccgaact ggacaaagca ggcttcatca agcgacagct ggtggagaca 2820
aggcagatca caaagcacgt cgctcagatc ctggacagca ggatgaacac caagtacgat 2880
gagaatgaca aactgatccg ggaagtgaag gtcattacac tgaagtcaaa actggtgagc 2940
gactttagga aagatttcca gttctacaag gtcagagaga tcaacaacta ccaccatgct 3000
catgacgcat acctgaacgc agtggtcggg actgccctga ttaagaaata ccctaaactg 3060
gagtctgagt tcgtgtacgg cgactataag gtgtacgatg tcagaaaaat gatcgccaag 3120
agcgagcagg aaattggcaa agccaccgct aagtatttct tttactccaa catcatgaat 3180

-continued

```
ttctttaaga ctgagatcac cctggcaaat ggcgaaatcc gaaagaggcc actgattgag   3240

actaacggag agacagggga aatcgtgtgg gacaaaggaa gagattttgc taccgtgcgg   3300

aaggtcctga gtatgcccca agtgaatatt gtcaagaaaa cagaggtgca gactggaggg   3360

ttcagtaagg aatcaattct gcctaaacgc aacagcgata agctgatcgc ccgaaagaaa   3420

gactgggacc ccaagaagta tggcggattc gactccccaa ccgtggctta ctctgtcctg   3480

gtggtcgcaa aggtggagaa gggaaaaagc aagaaactga aatccgtcaa ggaactgctg   3540

gggatcacaa ttatggagag gagcagcttc gaaaagaatc ctatcgattt tctggaggcc   3600

aaagggtata aggaagtgaa gaaagacctg atcatcaagc tgccaaagta ctctctgttt   3660

gagctggaaa acggcagaaa gcggatgctg gcaagtgccg gcgagctgca aaaaggaaat   3720

gaactggccc tgccctcaaa gtacgtgaac ttcctgtatc tggctagcca ctacgagaag   3780

ctgaaaggct cccctgagga taacgaacag aaacagctgt ttgtggagca gcacaagcat   3840

tatctggacg agatcattga acagattagc gagttctcca aacgcgtgat cctggctgac   3900

gcaaatctgg ataaggtcct gtctgcatac aacaaacaca gggacaagcc aatcagagag   3960

caggccgaaa atatcattca tctgttcact ctgaccaacc tgggagcccc cgcagccttc   4020

aagtattttg acactaccat cgatcgcaaa cgatacacaa gcactaagga ggtgctggat   4080

gctaccctga tccaccagag cattactggg ctgtacgaga caaggatcga cctgtcccag   4140

ctgggggggag acaaacgccc agccgccacc aagaaagcag gacaggcaaa gaagaagaag   4200

tga                                                                 4203
```

```
<210> SEQ ID NO 5
<211> LENGTH: 4203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

atggccccaa agaagaagcg gaaggtcggt atccacggag tcccagcagc cgacaagaag     60

tacagcatcg gcctggacat cggcaccaac tctgtgggct gggccgtgat caccgacgag    120

tacaaggtgc ccagcaagaa attcaaggtg ctgggcaaca ccgaccggca cagcatcaag    180

aagaacctga tcggagccct gctgttcgac agcggcgaaa cagccgaggc cacccggctg    240

aagagaaccg ccagaagaag atacaccaga cggaagaacc ggatctgcta tctgcaagag    300

atcttcagca acgagatggc caaggtggac gacagcttct tccacagact ggaagagtcc    360

ttcctggtgg aagaggataa gaagcacgag cggcacccca tcttcggcaa catcgtggac    420

gaggtggcct accacgagaa gtaccccacc atctaccacc tgagaaagaa actggtggac    480

agcaccgaca aggccgacct gcggctgatc tatctggccc tggcccacat gatcaagttc    540

cggggccact tcctgatcga gggcgacctg aaccccgaca acagcgacgt ggacaagctg    600

ttcatccagc tggtgcagac ctacaaccag ctgttcgagg aaaaccccat caacgccagc    660

ggcgtggacg ccaaggccat cctgtctgcc agactgagca agagcagacg gctggaaaat    720

ctgatcgccc agctgcccgg cgagaagaag aatggcctgt tcggcaacct gattgccctg    780

agcctgggcc tgacccccaa cttcaagagc aacttcgacc tggccgagga tgccaaactg    840

cagctgagca aggacaccta cgacgacgac ctggacaacc tgctggccca gatcggcgac    900

cagtacgccg acctgtttct ggccgccaag aacctgtccg acgccatcct gctgagcgac    960
```

-continued

```
atcctgagag tgaacaccga gatcaccaag gccccccctga gcgcctctat gatcaagaga   1020
tacgacgagc accaccagga cctgaccctg ctgaaagctc tcgtgcggca gcagctgcct   1080
gagaagtaca aagagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcggaa gcagcggacc   1260
ttcgacaacg gcagcatccc ccaccagatc cacctgggag agctgcacgc cattctgcgg   1320
cggcaggaag atttttaccc attcctgaag gacaaccggg aaaagatcga gaagatcctg   1380
accttccgca tcccctacta cgtgggccct ctggccaggg gaaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga aatacgtgac cgagggaatg agaaagcccg ccttcctgag cggcgagcag   1680
aaaaaggcca tcgtggacct gctgttcaag accaaccgga aagtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatgagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg gctggggcag gctgagccgg   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccggcagccc cgccattaag aagggcatcc tgcagacagt gaaggtggtg   2280
gacgagctcg tgaaagtgat gggccggcac aagcccgaga acatcgtgat cgaaatggcc   2340
agagagaacc agaccaccca gaagggacag aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccatat cgtgcctcag   2580
agctttctga aggacgactc catcgacaac aaggtgctga ccagaagcga caagaaccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaaagta ccctaagctg   3060
gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgagattac cctggccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
```

-continued ttcagcaaag agtctatcct gcccaagagg aacagcgata agctgatcgc cagaaagaag 3420
gactgggacc ctaagaagta cggcggcttc gacagcccca ccgtggccta ttctgtgctg 3480
gtggtggcca aagtggaaaa gggcaagtcc aagaaactga agagtgtgaa agagctgctg 3540
gggatcacca tcatggaaag aagcagcttc gagaagaatc ccatcgactt tctggaagcc 3600
aagggctaca aagaagtgaa aaaggacctg atcatcaagc tgcctaagta ctccctgttc 3660
gagctggaaa acggccggaa gagaatgctg gcctctgccg gcgaactgca gaagggaaac 3720
gaactggccc tgccctccaa atatgtgaac ttcctgtacc tggccagcca ctatgagaag 3780
ctgaagggct cccccgagga taatgagcag aaacagctgt ttgtggaaca gcacaagcac 3840
tacctggacg agatcatcga gcagatcagc gagttctcca agagagtgat cctggccgac 3900
gctaatctgg acaaagtgct gtccgcctac aacaagcacc gggataagcc catcagagag 3960
caggccgaga atatcatcca cctgtttacc ctgaccaatc tgggagcccc tgccgccttc 4020
aagtactttg acaccaccat cgaccggaag aggtacacca gcaccaaaga ggtgctggac 4080
gccaccctga tccaccagag catcaccggc ctgtacgaga cacggatcga cctgtctcag 4140
ctgggaggcg acaagcgtcc tgctgctact aagaaagctg gtcaagctaa gaaaaagaaa 4200
tga 4203

<210> SEQ ID NO 6
<211> LENGTH: 131
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
gggaatctta taagttctgt atgagaccac ttggatcctc tggtctctgt tttagagcta 60
gaaatagcaa gttaaaataa ggctagtccg ttatcaactt gaaaaagtgg caccgagtcg 120
gtgctttttt t 131

<210> SEQ ID NO 7
<211> LENGTH: 132
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
aaaaaaaagc accgactcgg tgccactttt tcaagttgat aacggactag ccttatttta 60
acttgctatt tctagctcta aaacagagac cagaggatcc aagtggtctc atacagaact 120
tataagattc cc 132

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (16)..(35)
<223> OTHER INFORMATION: a, c, t, g, unknown or other

<400> SEQUENCE: 8
tgtatgagac cacttnnnnn nnnnnnnnnn nnnnn 35

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (5)..(27)
<223> OTHER INFORMATION: a, c, t, g, unknown or other

<400> SEQUENCE: 9
aaacnnnnnn nnnnnnnnnn nnnnnnnaag tggtctca 38

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 10
nnnnnnnnnn nnnnnnnnnn ngg 23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
ggggccacta gggacaggat 20

<210> SEQ ID NO 12
<211> LENGTH: 252
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
tcagccgcta ccccgaccac atgaagcagc acgacttctt caagtccgcc atgcccgaag 60
gctacgtcca ggagcgcacc atcttcttca aggacgacgg caactacaag acctaagtcc 120
cctccacccc acagtggggc cactagggac aggattggtg acagaaaagc gcgccgaggt 180
gaagttcgag ggcgacaccc tggtgaaccg catcgagctg aagggcatcg acttcaagga 240
ggacggcaac at 252

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide -continued

```
<400> SEQUENCE: 13

ggcatgcgag aatctgacgc                                                20


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

catgccagag atcctatttt                                                20
```